(12) United States Patent
Haertle et al.

(10) Patent No.: US 10,774,154 B2
(45) Date of Patent: Sep. 15, 2020

(54) COMPLEX-SPECIFIC ANTIBODIES AND ANTIBODY FRAGMENTS AND ITS USE

(71) Applicant: MORPHOSYS AG, Planegg (DE)

(72) Inventors: Stefan Haertle, Mammendorf (DE); Christian Frisch, Munich (DE); Achim Knappik, Moorenweis (DE)

(73) Assignee: MORPHOSYS AG, Planegg (DE)

( * ) Notice: Subject to any disclaimer, the term of this patent is extended or adjusted under 35 U.S.C. 154(b) by 85 days.

(21) Appl. No.: 15/846,686

(22) Filed: Dec. 19, 2017

(65) Prior Publication Data

US 2018/0134807 A1 May 17, 2018

Related U.S. Application Data

(62) Division of application No. 14/418,089, filed as application No. PCT/EP2013/066625 on Aug. 8, 2013, now abandoned.

(60) Provisional application No. 61/684,836, filed on Aug. 20, 2012.

(51) Int. Cl.
  *C07K 16/42* (2006.01)
  *C07K 16/24* (2006.01)
  *G01N 33/68* (2006.01)

(52) U.S. Cl.
  CPC ........ *C07K 16/4241* (2013.01); *C07K 16/241* (2013.01); *C07K 16/243* (2013.01); *C07K 16/42* (2013.01); *G01N 33/686* (2013.01); *C07K 2317/30* (2013.01); *C07K 2317/32* (2013.01); *C07K 2317/55* (2013.01)

(58) Field of Classification Search
  CPC .. C07K 16/4241; C07K 16/243; C07K 16/42; C07K 2317/30; C07K 2317/32; C07K 2317/55; G07K 16/241; G01N 33/686
  See application file for complete search history.

(56) References Cited

U.S. PATENT DOCUMENTS

| 5,932,704 | A | 8/1999 | Jubinsky | 530/388.2 |
|---|---|---|---|---|
| 7,867,495 | B2 | 1/2011 | Steidl et al. | 424/141.1 |
| 2009/0068172 | A1* | 3/2009 | Kaymakcalan | C07K 16/4241 424/131.1 |
| 2010/0040605 | A1 | 2/2010 | Azuma et al. | 424/131.1 |
| 2010/0167307 | A1* | 7/2010 | Buechler | G01N 33/6887 435/7.1 |
| 2011/0195438 | A1 | 8/2011 | Kondou et al. | 435/7.92 |
| 2011/0236994 | A1 | 9/2011 | Albitar | |
| 2012/0157663 | A1 | 6/2012 | Azuma | |

FOREIGN PATENT DOCUMENTS

| JP | 58177921 | 10/1983 |
|---|---|---|
| JP | 2000055917 | 2/2000 |
| JP | 2005533236 | 11/2005 |
| WO | 2003/024993 | 3/2003 |
| WO | 2006066912 | 6/2006 |
| WO | 2009032128 | 3/2009 |
| WO | 2009142221 | 11/2009 |
| WO | 2011/010673 | 1/2011 |

OTHER PUBLICATIONS

Extended European Search Report dated Jun. 3, 2019 in corresponding application EP 19168061.0.
EP12180835.6 extended European Search Report dated Nov. 30, 2012.
AbD Serotech, "Human anti Adalimumab (drug/target complex) HCA206 Fab", Sep. 1, 2012.
AbD Serotech, "Human anti Adalimumab (drug/target complex) HCA207 IgG", Sep. 1, 2012.
PCT/EP2013/066625 International Search Report dated Dec. 5, 2013.
Tornetta, et al.: "Isolation of human anti-idiotypic antibodies by phage display for clinical immune response assays", Journal of Immunological Methods 328 (2007) 34-44, Sep. 4, 2007.
Charles, et al.: "Regulation of Cytokines, Cytokine Inhibitors, and Acute-Phase Proteins Following Anti-TNF-a Therapy in Rheumatoid Arthritis", J Immunol 1999;163;1521-1528.
Poster AbD Serotech, Härtle, et al.: "Fast Development of Highly Specific Fully Human Anti" Idiotypic Antibodies, Poster for Ab Engineering, Ab Therapetics, Dec. 6, 2009.
AbD Serotech, brochure 2012, "Anti-Idiotypic Antibodies Supporting the Development of Human Antibody Therapeutics & Preclinical Research".
Kuang B. 2010 Bioanalysis, 2(6):1125-40.
Machine Translation of JP2000055917A 10 pages Feb. 25, 2000.
Morphosys, MorphoSys Strengthens Patent Position on Lead Program MOR103, retrieved from https://www.morphosys.com/media-investors/media-center/morphosys-strengthens-patent-position-on-lead-program-mor103, 3 pages May 15, 2017.
Office Communication dated Sep. 2, 2015 in U.S. Appl. No. 14/418,089, filed Jan. 29, 2015.
Office Communication dated Feb. 23, 2016 in U.S. Appl. No. 14/418,089, filed Jan. 29, 2015.
Office Communication dated Aug. 1, 2016 in U.S. Appl. No. 14/418,089, filed Jan. 29, 2015.
Office Communication dated Sep. 26, 2016 in U.S. Appl. No. 14/418,089, filed Jan. 29, 2015.
Office Communication dated Feb. 13, 2017 in U.S. Appl. No. 14/418,089, filed Jan. 29, 2015.

(Continued)

*Primary Examiner* — Andrea S Grossman
(74) *Attorney, Agent, or Firm* — Licata & Tyrrell P.C.

(57) ABSTRACT

The present invention provides antibodies and fragments thereof that specifically detect the complex of a specific cognate antigen-binding moiety, in particular antibodies, and its antigen. The antibodies of the present disclosure do not bind either said cognate antigen binding moiety or said antigen alone and this can be used e.g. to directly detect antigen-bound antigen-binding moieties. Further disclosed are methods for production and use of said antibodies and antibody fragments.

6 Claims, 8 Drawing Sheets

Specification includes a Sequence Listing.

(56) References Cited

OTHER PUBLICATIONS

Office Communication dated May 23, 2017 in U.S. Appl. No. 14/418,089, filed Jan. 29, 2015.
Office Communication dated Aug. Sep. 20, 2017 in U.S. Appl. No. 14/418,089, filed Jan. 29, 2015.
Office Communication dated Dec. 12, 2017 in U.S. Appl. No. 14/418,089, filed Jan. 29, 2015.

* cited by examiner

SEQUENCE LISTING

```
<160> NUMBER OF SEQ ID NOS: 30

<210> SEQ ID NO 1
<211> LENGTH: 10
<212> TYPE: PRT
<213> ORGANISM: Artificial Sequence
<220> FEATURE:
<223> OTHER INFORMATION: AdaTNF#1 HCDR1

<400> SEQUENCE: 1

Gly Gly Thr Phe Ser Thr Tyr Ala Ile Ser
1               5                   10

<210> SEQ ID NO 2
<211> LENGTH: 20
<212> TYPE: PRT
<213> ORGANISM: Artificial Sequence
<220> FEATURE:
<223> OTHER INFORMATION: AdaTNF#1 HCDR2

<400> SEQUENCE: 2

Trp Met Gly Gly Ile Ile Pro Ile Phe Gly Thr Ala Asn Tyr Ala Gln
1               5                   10                  15

Lys Phe Gln Gly
            20

<210> SEQ ID NO 3
<211> LENGTH: 17
<212> TYPE: PRT
<213> ORGANISM: Artificial Sequence
<220> FEATURE:
<223> OTHER INFORMATION: AdaTNF#1 HCDR3

<400> SEQUENCE: 3

Asp Tyr Phe Ser Ser Ile Gly Trp Val Val Tyr Tyr Gly Pro Met Asp
1               5                   10                  15

Tyr

<210> SEQ ID NO 4
<211> LENGTH: 12
<212> TYPE: PRT
<213> ORGANISM: Artificial Sequence
<220> FEATURE:
```

<223> OTHER INFORMATION: AdaTNF#1 LCDR1

<400> SEQUENCE: 4

Arg Ala Ser Gln Ser Val Ser Ser Pro Tyr Leu Ala
1               5                   10

<210> SEQ ID NO 5
<211> LENGTH: 11
<212> TYPE: PRT
<213> ORGANISM: Artificial Sequence
<220> FEATURE:
<223> OTHER INFORMATION: AdaTNF#1 LCDR2

<400> SEQUENCE: 5

Leu Leu Ile Tyr Asp Val Ser Ser Arg Ala Thr
1               5                   10

<210> SEQ ID NO 6
<211> LENGTH: 8
<212> TYPE: PRT
<213> ORGANISM: Artificial Sequence
<220> FEATURE:
<223> OTHER INFORMATION: AdaTNF#1 LCDR3

<400> SEQUENCE: 6

Gln Gln Tyr Thr Ser Thr Pro Pro
1               5

<210> SEQ ID NO 7
<211> LENGTH: 110
<212> TYPE: PRT
<213> ORGANISM: Artificial Sequence
<220> FEATURE:
<223> OTHER INFORMATION: AdaTNF#1 VL

<400> SEQUENCE: 7

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Pro
                20                  25                  30

Tyr Leu Ala Trp Tyr Gln Lys Pro Gly Gln Ala Pro Arg Leu Leu
        35                  40                  45

Ile Tyr Asp Val Ser Ser Arg Ala Thr Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Tyr Thr Ser Thr Pro
                85                  90                  95

Pro Thr Phe Gly Gln Gly Thr Lys Val Glu Ile Lys Arg Thr
            100                 105                 110

<210> SEQ ID NO 8
<211> LENGTH: 126
<212> TYPE: PRT
<213> ORGANISM: Artificial Sequence
<220> FEATURE:
<223> OTHER INFORMATION: AdaTNF#1 VH

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Phe Ser Ser Ile Gly Trp Val Val Tyr Tyr Gly Pro
            100                 105                 110

Met Asp Tyr Trp Gly Gln Gly Thr Leu Val Thr Val Ser Ser
        115                 120                 125

<210> SEQ ID NO 9
<211> LENGTH: 330
<212> TYPE: DNA
<213> ORGANISM: Artificial Sequence
<220> FEATURE:
<223> OTHER INFORMATION: AdaTNF#1 VL

<400> SEQUENCE: 9
gatatcgtgc tgacccagag cccggcgacc ctgagcctga gcccgggtga acgtgccacc      60
ctgagctgca gagcgagcca gtctgttttct tctccgtacc tggcttggta ccagcagaaa    120
ccgggccagg ccccgcgtct attaatctac gacgtttctt ctcgtgcgac cggcattccg    180
gcgcgtttta gcggcagcgg atccggcacc gatttcaccc tgaccattag cagcctggaa    240
ccggaagact ttgcggtgta ttattgccag cagtacactt ctactccgcc gacctttggc    300
cagggcacga agttgaaat taaacgtacg                                       330

<210> SEQ ID NO 10
<211> LENGTH: 378
<212> TYPE: DNA
<213> ORGANISM: Artificial Sequence
<220> FEATURE:
<223> OTHER INFORMATION: AdaTNF#1 VH

<400> SEQUENCE: 10
caggtgcaat tggtgcagag cggtgccgaa gtgaaaaaac cgggcagcag cgtgaaagtt      60
agctgcaaag catccggagg gacgttttct acttacgcta tctcttgggt gcgccaggcc    120
ccgggccagg gcctcgagtg gatgggcggt atcatcccga tcttcggcac tgcgaactac    180
gcccagaaat tcagggccgg ggtgaccatt accgccgatg aaagcaccag caccgcctat    240
atggaactga gcagcctgcg cagcgaagat acggccgtgt attattgcgc gcgtgactac    300
ttctcttcta tcggttgggt tgtttactac ggtccgatgg attactgggg ccaaggcacc    360
ctggtgactg ttagctca                                                   378

<210> SEQ ID NO 11
<211> LENGTH: 10
<212> TYPE: PRT
<213> ORGANISM: Artificial Sequence
<220> FEATURE:
<223> OTHER INFORMATION: AdaTNF#5 HCDR1

<400> SEQUENCE: 11

Gly Gly Thr Phe Ser Thr Asn Ala Ile Ser
1               5                   10

```
<210> SEQ ID NO 12
<211> LENGTH: 20
<212> TYPE: PRT
<213> ORGANISM: Artificial Sequence
<220> FEATURE:
<223> OTHER INFORMATION: AdaTNF#5 HCDR2

<400> SEQUENCE: 12

Trp Met Gly Gly Ile Asn Pro His Leu Gly His Ala Asp Tyr Ala Gln
1               5                   10                  15

Lys Phe Gln Gly
            20

<210> SEQ ID NO 13
<211> LENGTH: 18
<212> TYPE: PRT
<213> ORGANISM: Artificial Sequence
<220> FEATURE:
<223> OTHER INFORMATION: AdaTNF#5 HCDR3

<400> SEQUENCE: 13

Gly Trp Tyr Tyr Ile Gly Ser Asn Pro Ser Met Tyr Pro Asn Tyr Phe
1               5                   10                  15

Asp Pro

<210> SEQ ID NO 14
<211> LENGTH: 11
<212> TYPE: PRT
<213> ORGANISM: Artificial Sequence
<220> FEATURE:
<223> OTHER INFORMATION: AdaTNF#5 LCDR1

<400> SEQUENCE: 14

Arg Ala Ser Gln Thr Ile Ser Ser Tyr Leu Asn
1               5                   10

<210> SEQ ID NO 15
<211> LENGTH: 11
<212> TYPE: PRT
<213> ORGANISM: Artificial Sequence
<220> FEATURE:
<223> OTHER INFORMATION: AdaTNF#5 LCDR2

<400> SEQUENCE: 15

Leu Leu Ile Tyr Thr Ala Ser Asn Leu Gln Ser
1               5                   10

<210> SEQ ID NO 16
<211> LENGTH: 8
<212> TYPE: PRT
<213> ORGANISM: Artificial Sequence
<220> FEATURE:
<223> OTHER INFORMATION: AdaTNF#5 LCDr3

<400> SEQUENCE: 16

Gln Gln Val Leu His Leu Pro His
1               5

<210> SEQ ID NO 17
<211> LENGTH: 109
<212> TYPE: PRT
<213> ORGANISM: Artificial Sequence
<220> FEATURE:
<223> OTHER INFORMATION: AdaTNF#5 VL

<400> SEQUENCE: 17
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
        35                  40                  45

Tyr Thr Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Val Leu His Leu Pro His
                85                  90                  95

Thr Phe Gly Gln Gly Thr Lys Val Glu Ile Lys Arg Thr
            100                 105

<210> SEQ ID NO 18
<211> LENGTH: 127
<212> TYPE: PRT
<213> ORGANISM: Artificial Sequence
<220> FEATURE:
<223> OTHER INFORMATION: AdaTNF#5 VH

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Asn
            20                  25                  30

Ala Ile Ser Trp Val Arg Gln Ala Pro Gly Gln Gly Leu Glu Trp Met
        35                  40                  45

Gly Gly Ile Asn Pro His Leu Gly His Ala Asp Tyr Ala Gln Lys Phe
    50                  55                  60

Gln Gly Arg Val Thr Ile Thr Ala Asp Glu Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Gly Trp Tyr Tyr Ile Gly Ser Asn Pro Ser Met Tyr Pro Asn
            100                 105                 110

Tyr Phe Asp Pro Trp Gly Gln Gly Thr Leu Val Thr Val Ser Ser
        115                 120                 125

<210> SEQ ID NO 19
<211> LENGTH: 327
<212> TYPE: DNA
<213> ORGANISM: Artificial Sequence
<220> FEATURE:
<223> OTHER INFORMATION: AdaTNF#5 VL

<400> SEQUENCE: 19
gatatccaga tgacccagag cccgagcagc ctgagcgcca gcgtgggcga tcgcgtgacc     60
attacctgca gagccagcca gactatttct tcttacctga actggtacca gcagaaaccg    120
ggcaaagcgc cgaaactatt aatctacact gcttctaacc tgcaaagcgg cgtgccgagc    180
cgctttagcg gcagcggatc cggcaccgat ttcaccctga ccattagctc tctgcaaccg    240
gaagactttg cgacctatta ttgccagcag gttctgcatc tgccgcatac ctttggccag    300
ggcacgaaag ttgaaattaa acgtacg                                        327

<210> SEQ ID NO 20

<211> LENGTH: 381
<212> TYPE: DNA
<213> ORGANISM: Artificial Sequence
<220> FEATURE:
<223> OTHER INFORMATION: AdaTNF#5 VH

<400> SEQUENCE: 20

```
caggtgcaat tggtgcagag cggtgccgaa gtgaaaaaac cgggcagcag cgtgaaagtt      60
agctgcaaag catccggagg gacgttttct actaacgcta tctcttgggt gcgccaggcc     120
ccgggccagg gcctcgagtg gatgggcggt atcaacccgc atctgggcca tgcggactac     180
gcccagaaat ttcagggccg ggtgaccatt accgccgatg aaagcaccag caccgcctat     240
atggaactga gcagcctgcg cagcgaagat acggccgtgt attattgcgc gcgtggttgg     300
tactacatcg ttctaacccc gtctatgtac ccgaactact tcgatccgtg gggccaaggc     360
accctggtga ctgttagctc a                                               381
```

<210> SEQ ID NO 21
<211> LENGTH: 10
<212> TYPE: PRT
<213> ORGANISM: Artificial Sequence
<220> FEATURE:
<223> OTHER INFORMATION: IFX-TNF#1 HCDR1

<400> SEQUENCE: 21

Gly Phe Thr Phe Ser Ser Tyr Gly Met His
1               5                   10

<210> SEQ ID NO 22
<211> LENGTH: 20
<212> TYPE: PRT
<213> ORGANISM: Artificial Sequence
<220> FEATURE:
<223> OTHER INFORMATION: IFX-TNF#1 HCDR2

<400> SEQUENCE: 22

Trp Val Ser Tyr Ile Tyr Tyr Gly Gly Ser Asp Thr Tyr Tyr Ala Asp
1               5                   10                  15
Ser Val Lys Gly
            20

<210> SEQ ID NO 23
<211> LENGTH: 13
<212> TYPE: PRT
<213> ORGANISM: Artificial Sequence
<220> FEATURE:
<223> OTHER INFORMATION: IFX-TNF#1 HCDR3

<400> SEQUENCE: 23

Gly Met Tyr Tyr Leu Tyr Asp Gln Pro Ala Phe Asp Tyr
1               5                   10

<210> SEQ ID NO 24
<211> LENGTH: 11
<212> TYPE: PRT
<213> ORGANISM: Artificial Sequence
<220> FEATURE:
<223> OTHER INFORMATION: IFX-TNF#1 LCDR1

<400> SEQUENCE: 24

Ser Gly Asp Asn Ile Arg Ser Asp Tyr Val His
1               5                   10

<210> SEQ ID NO 25

```
<211> LENGTH: 11
<212> TYPE: PRT
<213> ORGANISM: Artificial Sequence
<220> FEATURE:
<223> OTHER INFORMATION: IFX-TNF#1 LCDR2

<400> SEQUENCE: 25

Leu Val Ile Tyr Asp Lys Ser Glu Arg Pro Ser
1               5                   10

<210> SEQ ID NO 26
<211> LENGTH: 10
<212> TYPE: PRT
<213> ORGANISM: Artificial Sequence
<220> FEATURE:
<223> OTHER INFORMATION: IFX-TNF#1 LCDR3

<400> SEQUENCE: 26

Gln Ala Ala Asp Thr Trp Ser Thr Ile Val
1               5                   10

<210> SEQ ID NO 27
<211> LENGTH: 109
<212> TYPE: PRT
<213> ORGANISM: Artificial Sequence
<220> FEATURE:
<223> OTHER INFORMATION: IFX-TNF#1 VL

<400> SEQUENCE: 27

Asp Ile Glu Leu Thr Gln Pro Pro Ser Val Ser Val Ala Pro Gly Gln
1               5                   10                  15

Thr Ala Arg Ile Ser Cys Ser Gly Asp Ser Leu Gly Asp Tyr Tyr Val
                20                  25                  30

His Trp Tyr Gln Gln Lys Pro Gly Gln Ala Pro Val Leu Val Ile Tyr
            35                  40                  45

Ala Asp Asn Asn Arg Pro Ser Gly Ile Pro Glu Arg Phe Ser Gly Ser
        50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Thr Tyr Asp Arg Ser Ser Pro
                85                  90                  95

Val Phe Gly Gly Gly Thr Lys Leu Thr Val Leu Gly Gln
            100                 105

<210> SEQ ID NO 28
<211> LENGTH: 115
<212> TYPE: PRT
<213> ORGANISM: Artificial Sequence
<220> FEATURE:
<223> OTHER INFORMATION: IFX-TNF#1 VH

<400> SEQUENCE: 28

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
                20                  25                  30

Ala Met Ser Trp Val Arg Gln Ala Pro Gly Lys Gly Leu Glu Trp Val
            35                  40                  45

Ser Gly Ile Gly Ser Tyr Thr Tyr Tyr Ala Asp Ser Val Lys Gly Arg
        50                  55                  60

Phe Thr Ile Ser Arg Asp Asn Ser Lys Asn Thr Leu Tyr Leu Gln Met
65                  70                  75                  80
```

```
Asn Ser Leu Arg Ala Glu Asp Thr Ala Val Tyr Tyr Cys Ala Arg Leu
                85                  90                  95

Ser Gln Thr Gly Val Met Asp Tyr Trp Gly Gln Gly Thr Leu Val Thr
            100                 105                 110

Val Ser Ser
        115

<210> SEQ ID NO 29
<211> LENGTH: 327
<212> TYPE: DNA
<213> ORGANISM: Artificial Sequence
<220> FEATURE:
<223> OTHER INFORMATION: IFX-TNF#1 VL

<400> SEQUENCE: 29
gatatcgaac tgacccagcc gccttcagtg agcgttgcac caggtcagac cgcgcgtatc      60
tcgtgtagcg gcgattctct tggtgattat tatgttcatt ggtaccagca gaaacccggg     120
caggcgccag ttcttgtgat ttatgctgat aataatcgtc cctcaggcat cccggaacgc     180
tttagcggat ccaacagcgg caacaccgcg accctgacca ttagcggcac tcaggcggaa     240
gacgaagcgg attattattg ccagacttat gatgatcgtt cttctcctgt gtttggcggc     300
ggcacgaagt taaccgtcct aggtcag                                          327

<210> SEQ ID NO 30
<211> LENGTH: 345
<212> TYPE: DNA
<213> ORGANISM: Artificial Sequence
<220> FEATURE:
<223> OTHER INFORMATION: IFX-TNF#1 VH

<400> SEQUENCE: 30
caggtgcaat tggtggaaag cggcggcggc ctggtgcaac cgggcggcag cctgcgtctg      60
agctgcgcgg cctccggatt tacctttaat tcttatgcta tgtcttgggt gcgccaagcc     120
cctgggaagg gtctcgagtg ggtgagcggt atcggtagct atacctatta tgcggatagc     180
gtgaaaggcc gttttaccat ttcacgtgat aattcgaaaa acaccctgta tctgcaaatg     240
aacagcctgc gtgcggaaga tacggccgtg tattattgcg cgcgtctttc tcagactggt     300
gttatggatt attggggcca aggcacccta gtgacggtta gctca                     345
```

COMPLEX-SPECIFIC ANTIBODIES AND ANTIBODY FRAGMENTS AND ITS USE

CROSS REFERENCE TO RELATED APPLICATIONS

This application is a divisional of U.S. application Ser. No. 14/418,089, filed Jan. 29, 2015, which is the U.S. National Stage of PCT/EP2013/066625, filed Aug. 8, 2013, which claims the benefit of U.S. Provisional Application Ser. No. 61/684,836 filed Aug. 20, 2012, each of which is incorporated by reference in its entirety.

BACKGROUND OF THE INVENTION

Immunoglobulins, such as antibodies, are of continued and increasing interest for the pharmaceutical industry. Since 2000, the therapeutic market for monoclonal antibodies has grown exponentially and in 2007, eight of the 20 best-selling biotechnology drugs in the U.S. were therapeutic monoclonal antibodies each having world wide annual sales of more than 5 billion USD.

Currently, a significant number of antibodies and also derivatives and fragments of immunoglobulins are in pre-clinical and clinical development. Before entry into humans, the drug under investigation has to be analysed and characterized in extensive discovery and pre-clinical testing. Important criteria like toxicological, pharmacokinetic and pharmacodynamic characteristics need to be explored for the establishment of a safe and potent drug profile. In order to quantify and monitor the therapeutic antibody levels, many of these studies require the use of drug-specific agents for the specific detection of the therapeutic antibody in a sample matrix like e.g. the sera or any body liquid from a patient or an experimental animal.

Drug-specific agents include e.g. antibodies that only detect human or humanized immunoglobulin and can therefore be used to quantify a human or humanized therapeutic antibody in a sample derived from a non-human experimental host (see e.g. WO2006066912; U.S. Ser. No. 11/792,910 which is incorporated by reference in its entirety). One step further is the use of anti-idiotypic antibodies or antibody fragments, which are specific for a unique structure within the therapeutic antibody. Therefore, anti-idiotypic antibodies can be used to detect a specific therapeutic antibody or antibody fragment in a sample matrix irrespective of the host the sample is isolated from (see e.g. WO2009032128). However, because the vast majority of anti-idiotypic antibodies bind to one or more of the unique CDRs of the therapeutic antibody and the CDRs define the paratope that specifically interacts with the antigen of the therapeutic antibody, only the detection and monitoring of free, non antigen-bound therapeutic antibodies are possible.

US 2012/0157663 describes so-called "domino antibodies" which have the capacity to bind to an antibody only if the antibody is bound to the respective antigen. The antibodies of US 2012/0157663 are generated via a specific hybridoma-based screening technology. Common to all domino antibodies is that the epitope of the domino antibody on the target antibody is formed through a conformational change upon binding of the target antibody to its respective antigen. The epitope is located in the constant region of the target antibody (e.g. the constant region of the light chain) and does not include any parts of the antigen nor the CDR region of the target antibody. In contrast, the complex-specific antibodies and antibody fragments of the present invention bind to at least certain parts of the CDR regions of the target antibody. Therefore, although domino antibodies only recognize target antibodies when the target antibodies are bound to their respective antigen, domino antibodies also bind to other target antibodies with the same antigen specificity, i.e. they are pan-specific in this respect. In contrast, the antibodies and antibody fragments of the present invention are specific for one single target antibody, and they only bind to this target antibody when the target antibody has bound to its antigen.

Since a therapeutic antibody that was applied to a patient is always balanced between different states within the periphery of the host's body, the monitoring and proportion of these different states provides mandatory information for the safety of the therapeutic antibody. These different states are balanced according to the law of mass action and comprise total antibody, unbound antibody and bound antibody and said balance is dependent e.g. on the affinity of the therapeutic antibody and also the concentration of the antigen in the body. Furthermore, due to the relatively slow clearance of therapeutic antibodies from the body, the therapeutic antibody bound to its antigen often leads to an increase of antigen levels upon its administration for a longer term (Charles P. (1999) *Journal of Immunology* 163; 1521-1528). In the presence of the therapeutic antibody the bound antigen is neutralized and predominantly is not bio-active. However, this phenomenon must be monitored and is important e.g. to assess the risk of an abrupt withdrawal of the drug.

Taken together the specific detection of total antibody, unbound antibody and bound antibody is of particular interest and importance for the profiling and later approval of a therapeutic antibody (Kuang B. (2010) *Bioanalysis*, 2(6): 1125-40). Only a few anti-idiotypic antibodies are exemplified which are able to bind to the unbound therapeutic antibody and are also able to bind to the complex (therapeutic antibody bound to its antigen) and therefore are useful to detect the total antibody load. Such a non-paratopic anti-idiotypic antibody is disclosed in WO2009032128.

In contrast, almost all anti-idiotypic antibodies are directed to the CDRs of the target antibody and therefore only detect unbound antibody (see e.g. Tornetta M. (2007) *Journal of Immunological Methods* 328, 34-44).

However, neither the use of the CDR-specific anti-idiotypic antibody nor the use of the non-paratopic anti-idiotypic antibody enables the direct detection and quantification of the drug-antigen complex only. In order to quantify the bound antibody, various ELISA-based assays are established but always require the use of secondary, e.g. anti-human Fc, antibodies for indirect detection. The use of Fc-specific detection antibodies requires an extra step and extensive washing to capture and isolate the complex from the sera immunoglobulin and therefore these assays are susceptible for background noise and signal variations.

Accordingly alternative more sensitive and robust approaches are needed to detect and quantify antibody-antigen complexes.

SUMMARY OF THE INVENTION

The present invention discloses antibodies and antibody fragments that specifically detect and bind to the complex of a cognate antibody and its antigen. The antibodies of the present disclosure do not bind either said cognate antigen binding moiety or said antigen alone and thus can be used to directly detect bound therapeutic antibodies without using secondary Fc-specific antibodies.

The present invention also discloses antibodies and antibody fragments that specifically detect and bind to the complex of a specific cognate antibody and its antigen. In particular, the antibodies and antibody fragments of the present invention do not bind to the complex of other cognate antibodies with the same antigen specificity.

These complex-specific antibodies enable superior methods to quantify antibody-antigen complexes but also free or unbound drug in samples isolated from human patients or experimental animals. More sensitive and more robust assays, like e.g. ELISA set-ups, are disclosed herein and provide alternative and improved assays for pharmacokinetic studies. Furthermore, the quantification assays disclosed herein can be used to develop point of care tests using, for instance, lateral flow techniques to monitor drug levels.

The present disclosure further discloses the use of said antibodies in assays for the detection of said complexes. Furthermore, the present disclosure discloses methods to identify antibodies that specifically detect the complex of a specific cognate antibody and its antigen.

DETAILED DESCRIPTION OF THE INVENTION

Figure 1:
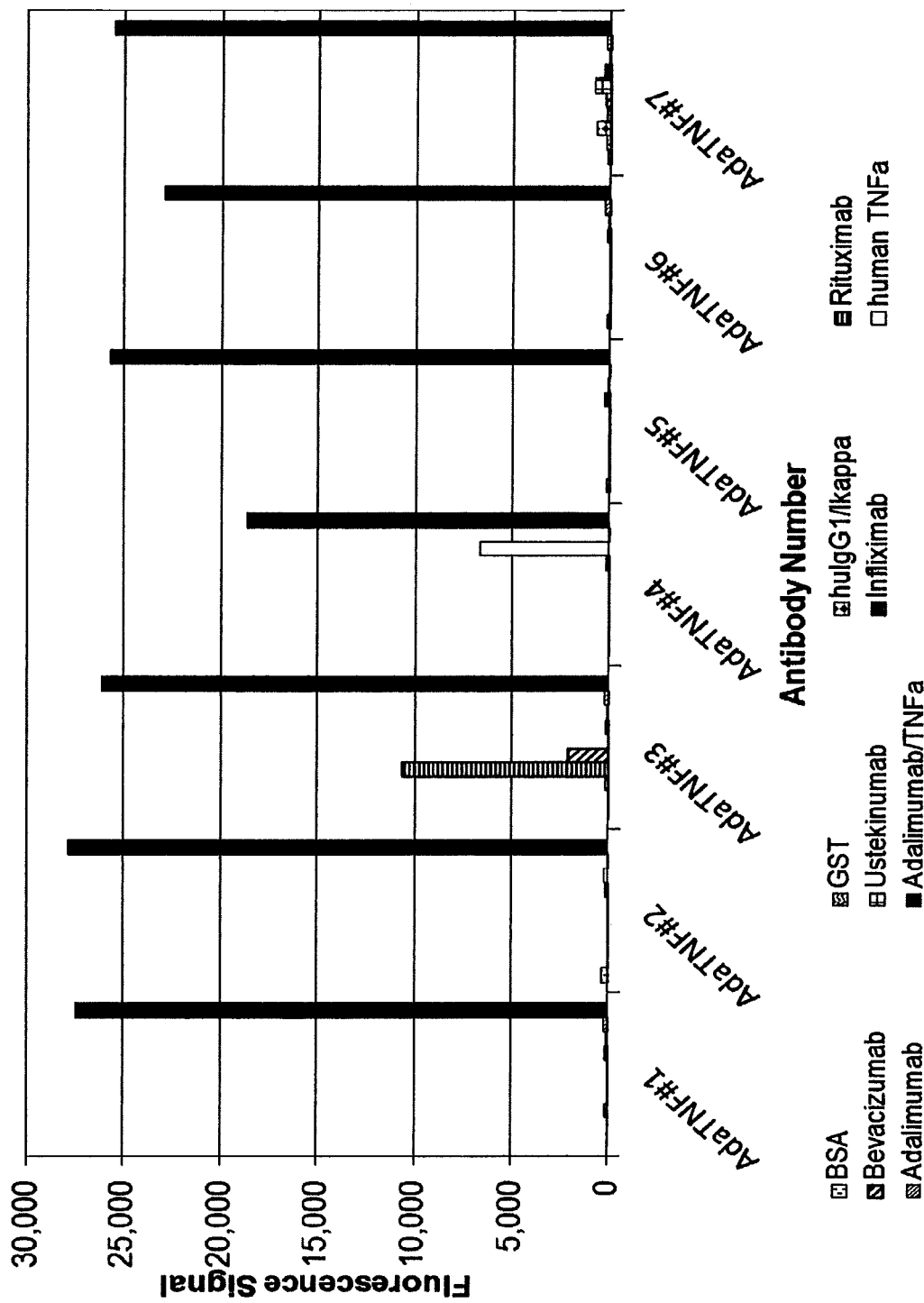
FIG. 1 depicts the results of 7 antibodies tested for specific binding in an ELISA against a series of unrelated and related antigens and the Adalimumab/TNF-α complex. 5 µg/mL of each of the antigens were coated on a microtiter plate over night. After washing and blocking with 5% BSA, anti-Adalimumab/TNF-α antibodies in Fab-FH format (20 µL from a 2 µg/mL solution) were added. Detection was performed using an HRP-labeled anti-His antibody and QuantaBlu fluorogenic peroxidase substrate.

Accordingly, in one aspect, the disclosure pertains to an isolated monoclonal antibody or fragment thereof, which specifically binds to the complex of a specific cognate antigen binding moiety and its antigen. In one embodiment the isolated monoclonal antibody or fragment thereof, specifically binds to the complex of a specific cognate antigen binding moiety and its antigen and does not bind either said cognate antigen-binding moiety or said antigen alone.

Isolated Monoclonal Antibody or Fragment Thereof

In another aspect, the disclosure pertains to an isolated monoclonal antibody or fragment thereof wherein the isolated monoclonal antibody or fragment thereof specifically binds to the complex of a specific cognate antigen binding moiety and its antigen with an $EC_{50}$ concentration of less than 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM or 1 nM.

In another aspect, the disclosure pertains to an isolated monoclonal antibody or fragment thereof wherein the isolated monoclonal antibody or fragment thereof specifically binds to the complex of a specific cognate antigen binding moiety and its antigen with a dissociation constant ($K_D$) of less than $1\times10^{-7}$ M$^{-1}$, $10^8$ M$^{-1}$, $10^9$ M$^{-1}$, $10^{10}$ M$^{-1}$, $10^{11}$ M$^{-1}$, $10^{12}$ m$^{-1}$ or $10^{13}$ M$^{-1}$.

In one aspect, the disclosure pertains to an isolated monoclonal antibody or fragment thereof wherein the isolated monoclonal antibody or fragment thereof is a monoclonal antibody or a polyclonal antibody. In one embodiment said isolated antibody or fragment thereof is a human or humanized antibody. In one embodiment said isolated antibody or fragment thereof is a chimeric antibody. In one embodiment said isolated antibody or fragment thereof comprises a human heavy chain constant region and a human light chain constant region. In one embodiment said isolated antibody is an IgG isotype. In another embodiment the antibodies can be of any isotype (e.g., IgG, IgE, IgM, IgD, and IgA), class (e.g., IgG1, IgG2, IgG3, IgG4, IgA1 and IgA2) or derivative thereof (e.g. IgG1f LALA). In one embodiment the antibodies are of IgG1f LALA isotype. In one embodiment said isolated antibody or fragment thereof is selected from the group consisting of a Fab, F(ab2)', F(ab)2' and scFV. In one embodiment the isolated antibody is selected from the group consisting of a monoclonal antibody, a polyclonal antibody, a chimeric antibody, a humanized antibody, and a synthetic antibody. In one embodiment, the antibody or fragment thereof is a human or humanized antibody.

The Cognate Antigen Binding Moiety

In one aspect, the disclosure pertains to an isolated monoclonal antibody or fragment thereof, which specifically binds to the complex of a cognate antigen binding moiety and its antigen. In another aspect, the disclosure pertains to an isolated monoclonal antibody or fragment thereof, which specifically binds to the complex of a specific cognate antigen binding moiety and its antigen. In one embodiment said cognate antigen binding moiety, or said specific cognate antigen binding moiety, is a cognate antibody or a fragment thereof. In one embodiment said cognate antibody or fragment thereof, or said specific cognate antibody or fragment thereof, is a therapeutic antibody or a therapeutic antibody fragment. In another embodiment said cognate antibody or fragment thereof, or said specific cognate antibody or fragment thereof, is a diagnostic antibody or a diagnostic antibody fragment.

In a preferred embodiment the cognate antibody or fragment thereof is a specific cognate monoclonal antibody or fragment thereof. A "specific cognate monoclonal antibody" refers to one, and only one, monoclonal antibody that specifically binds to its antigen. The target antibodies of so-called "domino antibodies" (see US 2012/0157663) are not specific cognate antibodies under this definition, since domino antibodies bind to the constant region of their target antibodies and therefore are not specific for one single antibody, but for all, or at least numerous, antibodies with a certain target specificity.

In a preferred embodiment the cognate antibody or fragment thereof is a cognate monoclonal antibody or fragment thereof.

In one embodiment said cognate monoclonal antibody or fragment thereof is a human or humanized antibody. In one embodiment said cognate monoclonal antibody or fragment thereof is a chimeric antibody. In one embodiment said cognate monoclonal antibody or fragment thereof comprises a human heavy chain constant region and a human light chain constant region. In one embodiment said cognate monoclonal antibody is an IgG isotype. In another embodiment the cognate antibodies can be of any isotype (e.g., IgG, IgE, IgM, IgD, and IgA), class (e.g., IgG1, IgG2, IgG3, IgG4, IgA1 and IgA2) or derivative thereof (e.g. IgG1f LALA). In one embodiment the cognate antibodies are of IgG1f LALA isotype.

In one embodiment said cognate monoclonal antibody or fragment thereof is selected from the group consisting of a Fab, F(ab2)', F(ab)2' and scFV. In one embodiment said cognate monoclonal antibody or fragment thereof is selected from the group consisting of a monoclonal antibody, a polyclonal antibody, a chimeric antibody, a humanized antibody, and a synthetic antibody. In one embodiment, the cognate antibody or fragment thereof is a human or humanized antibody.

In one aspect, the disclosure pertains to an isolated monoclonal antibody or fragment thereof, which specifically binds to the complex of a cognate antigen binding moiety and its antigen, or a specific cognate antigen binding moiety and its antigen, wherein the cognate antigen binding moiety is an antibody-derived scaffold. In one embodiment the antibody-derived scaffold is selected from the group consisting of a scFv, a tetravalent antibody, a cross-linked Fab or a IgG. In one embodiment, the cognate antibody or fragment thereof is a single chain antibody.

In one aspect, the disclosure pertains to an isolated monoclonal antibody or fragment thereof, which specifically binds to the complex of a cognate antigen binding moiety and its antigen, or the complex of a specific cognate antigen binding moiety and its antigen, wherein the cognate antigen binding moiety is selected from the group consisting of single domain antibodies, maxibodies, minibodies, intrabodies, diabodies, triabodies, tetrabodies, v-NAR, camelid antibodies, ankyrins, domain antibodies, lipocalins, small modular immuno-pharmaceuticals, maxybodies, Protein A and affilins.

In one aspect, the disclosure pertains to an isolated monoclonal antibody or fragment thereof, which specifically binds to the complex of a cognate antigen binding moiety and its antigen, or the complex of a cognate antigen binding moiety and its antigen, wherein the cognate antigen binding moiety is selected from a list that consists but is not limited to Adalimumab, MOR103, Rituximab, Trastuzumab, Alemtuzumab, Bevacizumab, Cetuximab, Gemtuzumab, Infliximab, Ranibizumab, Ustekinumab, Golimumab, Natalizumab, Ofatumumab, Omalizumab, Panitumumab.

The Antigen

In one aspect, the disclosure pertains to an isolated monoclonal antibody or fragment thereof, which specifically binds to the complex of a specific cognate antigen binding moiety and its antigen wherein the antigen is a protein. In a preferred embodiment the protein is a human protein.

The epitope of the isolated monoclonal antibody or fragment of the present invention includes one or more amino acids of a variable region of the specific cognate antibody. Therefore, in certain aspects the present disclosure pertains to an isolated monoclonal antibody or fragment thereof of, wherein the epitope of said isolated monoclonal antibody or fragment thereof includes one or more amino acids of a variable region of the specific cognate antibody. In other aspects, the present disclosure pertains to an isolated monoclonal antibody or fragment thereof, wherein the epitope of said isolated monoclonal antibody or fragment thereof includes one or more amino acids of a variable region of a specific cognate antibody and one or more amino acids of the antigen of said specific cognate antibody.

In other aspects, the present disclosure pertains to an isolated monoclonal antibody or fragment thereof, wherein the epitope of said isolated monoclonal antibody or fragment thereof includes stretches from both, a specific cognate antibody and the antigen of said specific cognate antibody.

In one embodiment the protein is associated with a specific disorder. In one embodiment the protein is a useful target for a specific biological therapy in a specific disorder. In one embodiment the protein is a useful target for a specific drug. In one embodiment the protein is a useful target for a therapeutic antibody or fragment thereof. In one embodiment the protein is a useful target for a diagnostic antibody or fragment thereof. In one embodiment the protein is a cytokine. In one embodiment the protein is a receptor.

In one embodiment the protein is associated with an inflammatory disease, autoimmune disease, viral, bacterial and parasitic infection, malignancy, neurodegenerative disease or any tumour-associated disease. In one embodiment the protein is associated with cancer.

In one embodiment In one embodiment the protein is selected from a list that consists but is not limited to TNF-α, TNF-β, VEGF-A, α4-integrin, CD20, IgE (Fc region), EGFR, GM-CSF, CD19, M-CSF, CD38, MIF, DDT, IL-17A, IL-17C, IL-1α, IL1-β, IL-6, IL-12, IL-23, Her2/c-neu, CD52, CD33.

In one aspect, the disclosure pertains to an isolated monoclonal antibody or fragment thereof, which specifically binds to the complex of a cognate antigen binding moiety and its antigen wherein the complex is selected from a group that consists but is not limited to Adalimumab/TNF-α, MOR103/GM-CSF, Trastuzumab/Her2/c-neu, Alemtuzumab/CD52, BevacizumabNEGF-A, Cetuximab/EGF-R, Gemtuzumab/CD33, Infliximab/TNF-α, Ranibizumab-NEGF-A, Ustekinumab/IL-12, Ustekinumab/IL-23, Golimumab/TNF-α, Natalizumab/α4-integrin, Ofatumumab/CD20, Rituximab/CD20, Omalizumab/IgE (Fc region), Panitumumab/EGFR.

Use of the Isolated monoclonal Antibody or Fragment Thereof

In one aspect, the disclosure pertains to the use of an isolated antibody or fragment thereof for the detection of a complex of a cognate antigen binding moiety and its antigen, or a complex of a specific cognate antigen binding moiety and its antigen, in a sample, wherein said isolated antibody or fragment thereof specifically binds to the complex of a cognate antigen binding moiety and its antigen, or the complex of a specific cognate antigen binding moiety and its antigen, and does not bind either said cognate antigen binding moiety or said antigen alone.

In another aspect, the disclosure pertains to a method of detecting the complex of a cognate antigen-binding moiety and its antigen, or the complex of a specific cognate antigen-binding moiety and its antigen, in a sample using an isolated antibody or fragment thereof which specifically binds to the complex of a cognate antigen binding moiety and its antigen, or to the complex of a cognate antigen binding moiety and its antigen, and does not bind either said cognate antigen binding moiety or said antigen alone.

In one aspect, the disclosure pertains to a method of detecting the complex of a cognate antigen-binding moiety and its antigen, or the complex of a specific cognate antigen-binding moiety and its antigen, in a sample, the method comprising the steps of
a) contacting said sample with an isolated antibody or fragment thereof wherein said isolated antibody or fragment thereof specifically binds said complex and does not bind either said cognate antigen binding moiety or said antigen alone
b) detecting said isolated antibody or fragment bound to said complex.

In another aspect, the disclosure pertains to a method of detecting the complex of a cognate antigen-binding moiety and its antigen, or a specific cognate antigen-binding moiety and its antigen, in a sample, the method comprising the steps of
a) contacting said sample with an isolated antibody or fragment thereof wherein said an isolated antibody or fragment thereof specifically binds said complex and does not bind either said cognate antigen binding moiety or said antigen alone
b) detecting said isolated antibody or fragment bound to said complex, and
c) correlating said isolated antibody or fragment bound to said complex with the concentration of the antigen-bound cognate antigen-binding moiety.

In another aspect, the disclosure pertains to a method of detecting the complex of a cognate antibody and its antigen, or the complex of a specific cognate antibody and its antigen, in a sample, the method comprising the steps of
a) providing the sample to be analysed,
b) contacting said sample with an isolated antibody or fragment thereof wherein said an isolated antibody or fragment thereof specifically binds said complex and does not bind either said cognate antibody or said antigen alone,
c) detecting said isolated antibody or fragment bound to said complex, and
d) correlating said isolated antibody or fragment bound to said complex with the concentration of the antigen-bound cognate antibody.

In one embodiment said cognate antigen binding moiety is a cognate antibody or fragment thereof. In a preferred embodiment the cognate antibody or fragment thereof is a cognate monoclonal antibody or fragment thereof. In one embodiment said cognate monoclonal antibody fragment thereof is a human or humanized antibody. In one embodiment said cognate monoclonal antibody fragment thereof is a chimeric antibody. In one embodiment said cognate monoclonal antibody fragment thereof comprises a human heavy chain constant region and a human light chain constant region. In one embodiment said cognate monoclonal antibody is an IgG isotype. In another embodiment the cognate antibodies can be of any isotype (e.g., IgG, IgE, IgM, IgD, and IgA), class (e.g., IgG1, IgG2, IgG3, IgG4, IgA1 and IgA2) or derivative thereof (e.g. IgG1f LALA). In one embodiment the cognate antibodies are of IgG1f LALA isotype.

In one embodiment said cognate monoclonal antibody fragment thereof is selected from the group consisting of a Fab, F(ab2)', F(ab)2' and scFV. In one embodiment said cognate monoclonal antibody fragment thereof is selected from the group consisting of a monoclonal antibody, a polyclonal antibody, a chimeric antibody, a humanized antibody, and a synthetic antibody. In one embodiment, the cognate antibody fragment thereof is a human or humanized antibody.

In one embodiment said complex of a specific cognate antibody and its antigen is selected from a group that consists but is not limited to Adalimumab/TNF-α, MOR103/GM-CSF, Trastuzumab/Her2/c-neu, Alemtuzumab/CD52, BevacizumabNEGF-A, Cetuximab/EGF-R, Gemtuzumab/CD33, Infliximab/TNF-α, Ranibizumab/VEGF-A, Ustekinumab/IL-12, Ustekinumab/IL-23, Golimumab/TNF-α, Natalizumab/α4-integrin, Ofatumumab/CD20, Rituximab/CD20, Omalizumab/IgE (Fc region), Panitumumab/EGFR.

In one aspect, the disclosure pertains to a method of detecting an antigen-binding moiety in a sample, the method comprising the steps of
a) immobilizing the antigen of the cognate antigen-binding moiety
b) bringing said immobilized antigen in contact with said sample
c) detecting the complex formed between said cognate antigen-binding moiety and its antigen with an isolated antibody or fragment thereof which specifically binds to said complex and does not bind either said cognate antigen binding moiety or said antigen alone.

In another aspect, the disclosure pertains to a method of detecting an unbound cognate antigen-binding moiety in a sample, the method comprising the steps of
a) immobilizing the antigen of the cognate antigen-binding moiety
b) bringing said immobilized antigen in contact with said sample
c) detecting the complex formed between said cognate antigen-binding moiety and its antigen with an isolated antibody or fragment thereof which specifically binds to said complex and does not bind either said cognate antigen binding moiety or said antigen alone.

In another aspect, the disclosure pertains to a method of detecting an unbound cognate antigen-binding moiety in a sample, the method comprising the steps of a) immobilizing the antigen of the cognate antigen-binding moiety b) bringing said immobilized antigen in contact with said sample c) detecting the complex formed between said cognate antigen-binding moiety and its antigen with an isolated antibody or fragment thereof which specifically binds to said complex and does not bind either said cognate antigen binding moiety or said antigen alone, and d) correlating the complex formed in b) with the concentration of the unbound cognate antigen-binding moiety in the sample.

In one embodiment the method, wherein said detection is accomplished by a means selected from the group consisting of EIA, ELISA, RIA, indirect competitive immunoassay, direct competitive immunoassay, non-competitive immunoassay, sandwich immunoassay, agglutination assay and MSD (Meso Scale Discovery). In a preferred embodiment said detection is accomplished by a sandwich ELISA. In another preferred embodiment said detection is accomplished by a MSD (Meso Scale Discovery) assay.

In one embodiment the sample is a tissue or a liquid sample. In a further embodiment the liquid sample is Saliva, urine, whole blood, plasma or serum. In a preferred embodiment the sample is obtained from an experimental animal or a human. In a more preferred embodiment the sample is whole blood, plasma or serum obtained from a human.

In one aspect, the disclosure pertains to a method to identify an isolated monoclonal antibody, or fragment thereof which specifically binds to the complex of a cognate antigen binding moiety and its antigen and does not bind either said cognate antigen binding moiety or said antigen alone, said method comprising (a) screening a library of antibodies or antibody fragments against a complex of a cognate antibody and its antigen, or a complex of a specific cognate antibody and its antigen, in the presence of the unbound antigen and an antibody that has the same isotype as the cognate antibody, (b) isolating said complex of a cognate antibody and its antigen, or said complex of a specific cognate antibody and its antigen, and the bound antigen-binding moiety, and (c) identifying and isolating said antigen-binding moiety.

In another aspect, the disclosure pertains to a method to identify an isolated monoclonal antibody, or fragment thereof which specifically binds to the complex of a cognate antigen binding moiety and its antigen and does not bind either said cognate antigen binding moiety or said antigen alone, said method comprising (a) screening a library of antibodies or antibody fragments against a complex of a cognate antibody and its antigen, or said complex of a specific cognate antibody and its antigen, in the presence of the unbound antigen and an antibody that has the same isotype and the same framework as the cognate antibody, (b) isolating said complex of a cognate antibody and its antigen, or said complex of a specific cognate antibody and its antigen, and the bound antigen-binding moiety, and (c) identifying and isolating said antigen-binding moiety.

In one aspect, the disclosure pertains to a kit comprising one or more antibodies, or fragments thereof, which specifically bind to the complex of a cognate antigen binding moiety and its antigen, or the complex of a specific cognate antigen binding moiety and its antigen, and do not bind either said cognate antigen binding moiety or said antigen alone and at least one reagent or device necessary for the detection of such a complex.

In another aspect, the disclosure pertains to a kit comprising one or more antibodies, or fragments thereof, which specifically bind to the complex of a cognate antigen binding moiety and its antigen, or the complex of a specific cognate antigen binding moiety and its antigen, and at least one reagent or device necessary for the detection of one or more different complexes of a cognate antigen binding moiety and its antigen of a specific cognate antigen binding moiety and its antigen. In another aspect, the disclosure pertains to a kit comprising an antibody or fragment thereof, which specifically binds to the complex of a cognate antigen binding moiety and its antigen, or the complex of a specific cognate antigen binding moiety and its antigen, and at least one reagent or device necessary for the detection of said complex. In one embodiment said device is a lateral flow device.

In another aspect, the disclosure pertains to a lateral flow device, comprising one or more antibodies, or fragments thereof, which specifically bind to the complex of a cognate antigen binding moiety and its antigen or to the complex of a specific cognate antigen binding moiety and its antigen. In one embodiment said one or more antibodies or fragments thereof, specifically bind to the complex of a cognate antigen binding moiety and its antigen, or to the complex of a specific cognate antigen binding moiety and its antigen, and do not bind either said cognate antigen binding moiety or said antigen alone. In a further embodiment said one or more antibodies are selected from the group of antibodies or fragments thereof which bind to one of the complexes selected from a group that consists but is not limited to Adalimumab/TNF-α, MOR103/GM-CSF, Trastuzumab/Her2/c-neu, Alemtuzumab/CD52, BevacizumabNEGF-A, Cetuximab/EGF-R, Gemtuzumab/CD33, Infliximab/TNF-α, RanibizumabNEGF-A, Ustekinumab/IL-12, Ustekinumab/IL-23,Golimumab/TNF-α, Natalizumab/α4-integrin, Ofatumumab/CD20, Rituximab/CD20, Omalizumab/IgE (Fc region), Panitumumab/EGFR.

In another aspect, the disclosure pertains to an isolated nucleic acid encoding a monoclonal antibody or fragment thereof, which specifically binds to the complex of a cognate antigen binding moiety and its antigen.

In another aspect, the disclosure pertains to a vector comprising an isolated nucleic acid encoding a monoclonal antibody or fragment thereof, which specifically binds to the complex of a cognate antigen binding moiety and its antigen.

In another aspect, the disclosure pertains to a host cell comprising a vector comprising an isolated nucleic acid encoding a monoclonal antibody or fragment thereof, which specifically binds to the complex of a cognate antigen binding moiety and its antigen. In one embodiment the host cell is a prokaryotic or eukaryotic host cell. In a preferred embodiment the host cell is a mammalian host cell.

In another aspect, the disclosure pertains to an isolated monoclonal antibody or fragment thereof that cross-competes with an antibody described in Table 1. In a certain embodiment, isolated monoclonal antibody or fragment thereof that cross-competes with an antibody described in Table 1 and reduces the specific binding of one of the antibodies described in Table 1 by at least 20%, 30%, 40%, 50%, 60%, 70%, 80% or 90% in an ELISA-based cross-competition.

In another aspect, the disclosure pertains to an isolated monoclonal antibody or fragment thereof that interacts with (e.g., by binding, stabilizing, spatial distribution) the same epitope as an antibody described in Table 1.

In one aspect, the disclosure pertains to an isolated monoclonal antibody or fragment thereof comprising 6 CDRs defined by Kabat of any of the antibodies in Table 1. In another aspect, the disclosure pertains to an isolated monoclonal antibody or fragment thereof comprising 6 CDRs defined by Kabat of each of the antibodies in Table 1.

In one aspect, the disclosure pertains to an isolated monoclonal antibody or fragment thereof comprising a VH and a VL of any of the antibodies in Table 1.

In another aspect, the disclosure pertains to a nucleic acid encoding an isolated monoclonal antibody or fragment thereof wherein the nucleic acid comprises a VH and a VL of any of the antibodies in Table 1.

In another aspect, the disclosure pertains to a nucleic acid encoding an isolated monoclonal antibody or fragment thereof having at least 75%, 80%, 85%, 90%, 95%, 98%, 99% sequence identity to nucleic acids described in Table 1.

Definitions

The term "antigen binding moiety", as used herein, refers to a moiety which comprises a polypeptide that confers the ability to specifically bind to a given antigen. For example, antibodies, antibody fragment, antibody derivatives, antibody-like scaffolds and alternative scaffolds comprise at least one antigen binding moiety. Antigen binding moieties can also be incorporated into single domain antibodies, maxibodies, minibodies, intrabodies, diabodies, triabodies, tetrabodies, v-NAR and scFv (see, e.g., Hollinger and Hudson, 2005, Nature Biotechnology, 23, 9, 1126-1136). Further examples of molecules comprising antigen binding moieties are given herein below and include fibronectin (Adnexus, fully owned by Bristol-Myers Squibb, Waltham, Mass.), camelid antibodies, ankyrins (Molecular Partners AG, Zurich, Switzerland), domain antibodies (Domantis, Ltd., Cambridge, Mass., and Ablynx nv, Zwijnaarde, Belgium), lipocalins (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilins (gamma-crystallin or ubiquitin) (Scil Proteins GmbH, Halle, Germany).

The term "antigen-binding region" as used herein refers to a domain of an antigen binding moiety that is responsible for the specific binding between an antigen binding moiety and an antigen. For example, the antigen-binding region of an antibody or a fragment thereof is formed by amino acid residues of the N-terminal variable regions of the heavy chain (abbreviated herein as VH) and the light chain (abbreviated herein as VL). The variable regions of the VH and the VL each comprise three hypervariable regions, termed complementary determining regions (CDR). The 3 CDRs of the VH and the 3 CDRs of the VL are three-dimensionally disposed relative to each other to form an antigen binding surface.

The term "antibody" as used herein includes whole antibodies and any fragment or single chains thereof. A naturally occurring "antibody" is a protein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementary determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The constant regions of the antibodies may mediate the binding of the immunoglobulin to host tissues or factors, including various cells of the immune system (e.g., effector cells) and the first component (C1q) of the classical complement system. The antibodies can be of any isotype (e.g., IgG, IgE, IgM, IgD, IgA and IgY), class (e.g., IgG1, IgG2, IgG3, IgG4, IgA1 and IgA2), subclass or modified version thereof (e.g. IgG1f LALA).

The term "fragment" of an antibody refers to one or more fragments of an antibody that retain the ability to specifically bind to an antigen. Examples of binding fragments encompassed within the term "fragment" include a Fab fragment, a monovalent fragment consisting of the VL, VH, CL and CH1 domains; a F(ab)$_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., (1989) Nature 341: 544-546), which consists of a VH domain; and an isolated complementary determining region (CDR) and a single chain Fragment (scFv) in which the VL and VH regions pair to form monovalent molecules (known as single chain Fv (scFv); see, e.g., Bird et al., (1988) Science 242:423-426; and Huston et al., (1988) Proc. Natl. Acad. Sci. 85:5879-5883). Although the two domains VL and VH are coded for by separate genes, they can be joined, using recombinant methods, by an artificial peptide linker that enables them to be made as a single protein chain. Such single chain antibodies include one or more antigen binding moieties. These antibody fragments are obtained using conventional techniques known to those of skill in the art, and the fragments are screened for utility in the same manner as are intact antibodies.

An "antigen" is defined as any molecule or complex of any molecules that is bound specifically by an antigen-binding moiety.

The term "complex" refers to an association between at least two moieties (e.g. chemical or biochemical) that have an affinity for one another. "Protein complex" or "polypeptide complex" refers to a complex comprising at least one or more polypeptides. As used herein, a complex comprises of a cognate antigen-binding moiety and its antigen. In one embodiment the complex is an antibody-antigen complex. In a preferred embodiment the complex is an antibody-antigen complex, comprising of a therapeutic antibody and its antigen The term "cognate" refers to components that function together, or have some aspect of specificity for each other, e.g., an orthogonal tRNA and an orthogonal aminoacyl-tRNA synthetase or an antibody and an antigen. The components can also be referred to as being complementary. As used herein, a cognate antigen-binding moiety is an antigen-binding moiety that specifically binds to its antigen.

The terms "heavy chain variable region CDR1" and "H-CDR1" are used interchangeably, as are the terms "heavy chain variable region CDR2" and "H-CDR2", the terms "heavy chain variable region CDR3" and "H-CDR3", the terms "light chain variable region CDR1" and "L-CDR1"; the terms "light chain variable region CDR2" and "L-CDR2" and the terms "light chain variable region CDR3" and "L-CDR3"

The term "human antibody", as used herein, is intended to include antibodies having variable regions in which both the framework and CDR regions are derived from sequences of human origin. As used herein, a human antibody comprises heavy or light chain variable regions or full length heavy or light chains. In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Thereby said human antibody can be obtained from technology platforms which comprise antibodies derived from human germline genes either generated by PCR-amplification of VH/VL repertoire isolated from B-cells or are generated synthetically. Technology platforms include library based approaches comprising human immunoglobulin genes displayed on phage, ribosome or yeast. Respective display technologies are standard in the scientific community. Furthermore immunization of a transgenic mouse carrying human immunoglobulin repertoire is another approach to generate human antibodies against an antigen of interest. Antibodies or fragments thereof selected from an antibody library based on the MorphoSys HuCAL® concept (Knappik et al., (2000) J Mol Biol 296:57-86) are considered as fully human.

The terms "monoclonal antibody" as used herein refer to a preparation of antibody molecules of single molecular composition. A monoclonal antibody composition displays a unique binding site having a unique binding specificity and affinity for particular epitopes.

A "humanized" antibody is an antibody that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al (1994) Proc. Natl. Acad. Sci. USA, 81:6851-6855; Morrison and Oi (1988) Adv. Immunol., 44:65-92; Verhoeyen et al. (1988) Science, 239:1534-1536; Padlan, Molec (1991) Immun., 28:489-498; and Padlan, Molec (1994) Immun., 31:169-217. Other examples of human engineering technology include, but are not limited to Xoma technology disclosed in U.S. Pat. No. 5,766,886.

The term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "isolated" refers to a compound which can be e.g. an antibody or an antigen binding moiety that is substantially free of other antibodies or antigen binding moieties having different antigenic specificities. Moreover, an isolated antibody antigen binding moiety may be substantially free of other cellular material and/or chemicals.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Unless otherwise indicated, a particular polypeptide sequence also implicitly encompasses conservatively modified variants thereof.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-$\alpha$ and -$\beta$; mullerian-inhibiting substance; mouse gonadotropin-associated peptide; inhibin; activin; vascular endothelial growth factor A-F (e.g. VEGF-A); integrin (e.g. $\alpha$4-integrin); thrombopoietin (TPO); nerve growth factors such as NGF-$\beta$; platelet-growth factor; transforming growth factors (TGFs) such as TGF-$\alpha$ and TGF-$\beta$; insulin-like growth factor-I and -II; erythropoietin (EPO); osteoinductive factors; interferons such as interferon-$\alpha$, -$\beta$, and -$\gamma$; colony stimulating factors (CSFs) such as macrophage-CSF (M-CSF); granulocyte-macrophage-CSF (GM-CSF); and granulocyte-CSF (G-CSF); interleukins (ILs) such as IL-I, IL-I$\alpha$, IL-2, IL-3, IL-4, IL-5, IL-6, IL-7, IL-8, IL-9, IL-11, IL-12, IL17-family members (e.g. IL-17C); a tumor necrosis factor such as TNF-$\alpha$ or TNF-$\beta$; and other polypeptide factors including LIF, kit ligand (KL), MIF, D-DT. As used herein, the term cytokine includes proteins from natural sources or from recombinant cell culture and biologically active equivalents of the native sequence cytokines.

The term "receptor" is a generic term for proteins having the ability to affect biological activity, in e.g., a cell, as a result of interaction with a specific ligand or binding partner. Cell membrane bound receptors are characterized by an extracellular ligand-binding domain, one or more membrane spanning or transmembrane domains, and an intracellular effector domain that is typically involved in signal transduction. Ligand binding to cell membrane receptors causes changes in the extracellular domain that are communicated across the cell membrane, direct or indirect interaction with one or more intracellular proteins, and alters cellular properties, such as enzyme activity, cell shape, or gene expression profile. Receptors may also be untethered to the cell surface and may be cytosolic, nuclear, or released from the cell altogether. In general, receptors can be membrane bound, cytosolic or nuclear; monomeric (e.g., thyroid stimulating hormone receptor, beta-adrenergic receptor) or multimeric (e.g., 'PDGF receptor, growth hormone receptor, IL-3 receptor, GM-CSF receptor, G-CSF I receptor, erythropoietin receptor and IL-6 receptor). More particular examples of receptors include, but are not limited to further clusters of differentiation (e.g. CD20, CD19, CD38, CD52, CD33), immunoglobulin (e.g. IgE (Fc region)), epidermal growth factor receptors (e.g. EGFR) or receptor tyrosine kinases (RTK)s (e.g. Her2/c-neu, Her3, Her4).

The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors. For example IgG1f LALA is a modified version of the IgG isotype having significantly reduced effector functions. Specific substitutions of amino acids reduced the binding affinity for Fc gamma RI receptor as compared with unmodified antibody. IgG1f LALA is described in U.S. Ser. No. 08/479,752 (SCOTGEN BIOPHARMACEUTICALS INC.) which is incorporated by reference in its entirety. In certain embodiments of the present disclosure the antigen-binding moieties of are antibodies and are of the type IgG, IgM, IgA, IGE or IgD. In specific embodiments the antibodies are of the type IgG. In certain embodiments of the present disclosure the antibodies are of the subtype IgG1, IgG2, IgG3 or IgG4. In specific embodiments the antibodies are of the subtype IgG1 or IgG4. In other specific embodiments the antibodies are of the subtype IgG1 or IgG1f LALA.

The phrase "specifically binds" to an antigen refers to a binding reaction that is determinable in the presence of an antigen in a heterogeneous population of proteins and other biologics. Thereby the phrases "recognizing an antigen" and "specific for an antigen" are used interchangeably herein with the term "binds specifically to an antigen". Specific binding of an antigen binding moiety, like e.g. a monoclonal antibody, to an antigen can be determined by various established methods known in the art and include ELISA, FACS, Western Blot, Immuno Blot, MSD, BIAcore and SET. In the present disclosure an antigen binding moiety is deemed to be specific for an antigen if the antigen binding moiety is demonstrated to be able to bind to a specific antigen at least 2-fold, at least 3-fold, at least 4-fold, at least 5-fold, at least 6-fold, at least 7-fold, at least 8-fold, at least 9-fold, at least 10-fold, at least 20-fold, at least 50-fold, at least 100-fold, at least 500-fold, at least 1000-fold over background. Thereby the background is determined by an antigen binding moiety which is known to be unspecific for the selected antigens or by comparison to binding to an unrelated antigen.

"Cross competes" means the ability of an antibody or other antigen-binding moieties to interfere with the binding of other antibodies or antigen-binding moieties to a specific antigen in a standard competitive binding assay. The ability or extent to which an antibody or other antigen-binding moieties is able to interfere with the binding of another antibody or antigen-binding moieties to a specific antigen, and, therefore whether it can be said to cross-compete according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-competing uses an ELISA-based approach. A high throughput process for "epitope binning" antibodies based upon their cross-competition is described in International Patent Application No. WO 2003/48731

The term "epitope" includes any protein determinant capable of specific binding to an antibody or otherwise interacting with a molecule. Epitopic determinants generally consist of chemically active surface groupings of molecules such as amino acids or carbohydrate or sugar side chains and can have specific three-dimensional structural characteristics, as well as specific charge characteristics. An epitope may be "linear" or "conformational." The term "linear epitope" refers to an epitope with all of the points of interaction between the protein and the interacting molecule (such as an antibody) occur linearly along the primary amino acid sequence of the protein (continuous). The term "conformational epitope" refers to an epitope in which discontinuous amino acids that come together in three dimensional conformation. In a conformational epitope, the points of interaction occur across amino acid residues on the protein that are separated from one another.

"Binds the same epitope as" means the ability of an antibody or other antigen-binding moiety to bind to a specific antigen and having the same epitope as the exemplified antibody. The epitopes of the exemplified antibody and other antibodies can be determined using epitope mapping techniques. Epitope mapping techniques are well known in the art. For example, conformational epitopes are readily identified by determining spatial conformation of amino acids such as by, e.g., hydrogen/deuterium exchange, x-ray crystallography and two-dimensional nuclear magnetic resonance.

The term "affinity" as used herein refers to the strength of interaction between an antigen binding moiety, like e.g. a monoclonal antibody and an antigen at single antigenic sites. Within each antigenic site, the variable region of the antibody "arm" interacts through weak non-covalent forces with antigen at numerous sites; the more interactions, the stronger the affinity.

The term "KD", as used herein, refers to the dissociation constant, which is obtained from the ratio of Kd to Ka (i.e. Kd/Ka) and is expressed as a molar concentration (M). KD values for antigen binding moieties like e.g. monoclonal antibodies can be determined using methods well established in the art. Methods for determining the KD of an antigen binding moiety like e.g. a monoclonal antibody are SET (soluble equilibrium titration) or surface plasmon resonance using a biosensor system such as a Biacore® system. In the present disclosure an antigen-binding moiety typically has a dissociation rate constant (KD) (koff/kon) of less than $5\times10^{-2}$M, less than $10^{-2}$M, less than $5\times10^{-3}$M, less than $10^{-3}$M, less than $5\times10^{-4}$M, less than $10^{-4}$M, less than $5\times10^{-5}$M, less than $10^{-5}$M, less than $5\times10^{-6}$M, less than $10^{-6}$M, less than $5\times10^{-7}$M, less than $10^{-7}$M, less than $5\times10^{-8}$M, less than $10^{-8}$M, less than $5\times10^{-9}$M, less than $10^{-9}$M, less than $5\times10^{-10}$M, less than $10_{-10}$M, less than $5\times10^{-11}$M, less than $10^{-11}$M, less than $5\times10^{-12}$M, less than $10^{-12}$M, less than $5\times10^{-13}$M, less than $10^{-13}$M, less than $5\times10^{-14}$M, less than $10^{-14}$M, less than $5\times10^{-15}$M, or less than $10^{-15}$M or lower.

A "disorder" is any condition that would benefit from medical treatment by using e.g. a therapeutic antibody or other antigen-binding moieties. Non-limiting examples of disorders include autoimmune disease, inflammation, cell proliferative disorders; B cell lymphomas, non-leukemias and lymphoid malignancies; neuronal, glial, astrocytal, hypothalamic and other glandular, macrophagal, epithelial, stromal and blastocoelic disorders; and inflammatory, immunologic, or infectious diseases. The terms "cell proliferative disorder" and "proliferative disorder" refer to disorders that are associated with some degree of abnormal cell proliferation. In one embodiment, the disorder is cancer.

As used herein, the term "autoimmune disease" refers generally to diseases which are characterized as having a component of self-recognition. Examples of autoimmune diseases include, but are not limited to, Autoimmune hepatitis, Multiple Sclerosis, Systemic Lupus Erythematosus, Idiopathic Thrombocytopenic Purpura, Myasthenia Gravis, Type I diabetes, Rheumatoid Arthritis, Psoriasis, Hashimoto's Thyroiditis, Grave's disease, Ankylosing Spondylitis Sjogrens Disease, CREST syndrome, Scleroderma, IgA Neprhopathy, Bullous Pemphigoid, Pemphigous Vulgaris, ANCA-Associated Vasculitis, Antiphospholipid Syndrome and many more. Most autoimmune diseases are also chronic inflammatory diseases. This is defined as a disease process associated with long-term (>6 months) activation of inflammatory cells (leukocytes). The chronic inflammation leads to damage of patient organs or tissues. Many diseases are chronic inflammatory disorders, but are not known to have an autoimmune basis. For example, Atherosclerosis, Congestive Heart Failure, Crohn's disease, Ulcerative Colitis, Polyarteritis nodosa, Whipple's Disease, Primary Sclerosing Cholangitis and many more.

The term "cancer" refers to the physiological condition in mammals that is typically characterized by unregulated cell growth/proliferation. Examples of cancer include, but are not limited to: carcinoma, lymphoma, blastoma, and leukemia. More particular examples of cancers include, but are not limited to: colorectal cancer, chronic lymphocytic leukemia (CLL), lung, including non small cell (NSCLC), breast, ovarian, cervical, endometrial, prostate, colorectal, intestinal carcinoid, bladder, gastric, pancreatic, hepatic (hepatocellular), hepatoblastoma, esophageal, pulmonary adenocarcinoma, mesothelioma, synovial sarcoma, osteosarcoma, head and neck squamous cell carcinoma, juvenile nasopharyngeal angiofibromas, liposarcoma, thyroid, melanoma, basal cell carcinoma (BCC), medulloblastoma and desmoid. Cancers of particular interest for treatment by the subject methods include gliomas, medulloblastomas, colon cancer, colorectal cancer, melanoma, breast cancer, lung cancer, liver cancer, and gastric cancer.

The term "therapeutic antibody" relates to any antibody preparation which is intended for use in a human being. Preferably such therapeutic antibody will be a monoclonal antibody. Further preferred such monoclonal antibody will be obtained from a great ape or be a human monoclonal antibody. Preferably, it will be a human monoclonal antibody. Also preferred such therapeutic monoclonal antibody will be a humanized monoclonal antibody. Therapeutic antibodies are being used widely for the treatment of various disorders such as oncological diseases (e.g. hematological and solid malignancies including non-Hodgkin's lymphoma, breast cancer, and colorectal cancer), immunological diseases, central nervous diseases, vascular diseases, or infectious diseases. Such antibodies are, in one embodiment antibodies against TNF-α, TNF-β, VEGF-A, α4-integrin, CD20, IgE (Fc region), EGFR, GM-CSF, CD19, M CSF, CD38, MIF, DDT, IL-17C, IL-12, Her2/c-neu, CD52, CD33. Such antibodies are e.g. Adalimumab, MOR103, Rituximab, Trastuzumab, Alemtuzumab, Bevacizumab, Cetuximab, Gemtuzumab, Infliximab, Ranibizumab, Ustekinumab, Golimumab, Natalizumab, Ofatumumab, Omalizumab, and Panitumumab.

The term "sample" as used within this application denotes, but is not limited to, any quantity of a substance from a living thing or formerly living thing. Such living things include, but are not limited to, humans, mice, monkeys, rats, rabbits, and other animals. Such substances include, but are not limited to, Saliva, urine, whole blood, serum or plasma from an individual. The most widely used sources of sample in clinical routine are whole blood, plasma or serum. In a preferred embodiment the sample was isolated from a patient. In more preferred embodiment the sample was isolated from a human.

The term "patient" as used herein denotes a mammal. Preferably, a patient according to the invention is a human.

As used herein, the term "bound" refers to binding or attachment that may be covalent, e.g., by chemically coupling, or non-covalent, e.g., ionic interactions, hydrophobic interactions, hydrogen bonds, etc. In a preferred embodiment the binding or attachment is a non-covalent interaction. In one example the term bound refers to the attachment of a cognate antigen binding moiety to its antigen The term "antigen-bound" antigen-binding moiety is used to indicate the antigen-binding moiety as present in the circulation of an experimental animal or a patient that is bound to its antigen. In a further embodiment the antigen-bound antigen-binding moiety is an antibody. In a further embodiment the antigen-bound antigen-binding moiety is a therapeutic antibody.

The term "unbound" antigen-binding moiety is used to indicate the antigen-binding moiety as present in the circulation of an experimental animal or a patient that is not bound to its antigen. In a further embodiment the antigen-binding moiety is an antibody or fragment thereof. In a further embodiment the antigen-binding moiety is a therapeutic antibody.

The term "collection" or "library" means at least two members. The term "member" includes, but is not limited to nucleic acids encoding antibodies or fragments thereof or the antibodies or fragments thereof themselves.

The term "library" refers to a set of entities comprising two or more entities having diversity as described herein. For example, a "library of antibodies or antibody fragments" refers to a set of polynucleotides comprising two or more polynucleotides encoding antibodies or antibody fragments and having diversity as described herein. For example the commercially available phage display libraries, like e.g. the MorphoSys HuCAL PLATINUM® library can be used.

As used herein, the term "diversity" refers to a variety or a noticeable heterogeneity.

The term "framework" means an antibody variable domain as defined by Kabat et al. (1991) as the part of the variable domain which serves as a scaffold for the antigen binding loops of this variable domain. Examples of the framework regions include FR1, FR2, FR3, and FR4 of either the variable heavy or variable light chains The term "isotype" refers to the antibody class (e.g., IgM, IgE, IgG such as IgG1 or IgG4) that is provided by the heavy chain constant region genes. Isotype also includes modified versions of one of these classes, where modifications have been made to alter the Fc function, for example, to enhance or reduce effector functions or binding to Fc receptors.

By an "anti-idiotypic antibody" is meant an antibody that specifically binds to the antigen-binding region of another antibody and, therefore, is specifically bound by the other antibody. The anti-idiotype antibody can mimic the epitope normally recognized by another antibody. An idiotype is the genetically determined variation of structures in the variable regions of immunoglobulins. The precise genetic basis of idiotype variability has only been partially explained. However, idiotype variation involves the amino acid sequence and protein structure (so-called determinants) especially in the area of the antigen-binding region, also referred to as the idiotope. The term "idiotype" designates the complete set of determinants of a variable region of an antibody molecule.

The term "amino acid" refers to naturally occurring and also synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260: 2605-2608; and Rossolini et al. (1994) Mol. Cell. Probes 8:91-98).

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "vector", as used herein, refers to a molecular vehicle used to transfer foreign genetic material into another cell. The vector itself is generally a DNA sequence that consists of an insert (sequence of interest) and a larger sequence that serves as the "backbone" of the vector. The purpose of a vector to transfer genetic information to another cell is typically to isolate, multiply, or express the insert in the target cell.

As used herein the term "lateral flow" refers to liquid flow along the plane of a substrate or carrier, e.g., a lateral flow membrane. In general, lateral flow devices comprise a strip (or a plurality of strips in fluid communication) of material capable of transporting a solution by capillary action, i.e., a wicking or chromatographic action, wherein different areas or zones in the strip(s) contain assay reagents, which are either diffusively or non-diffusively bound to the substrate, that produce a detectable signal as the solution is transported to or migrates through such zones. Typically, such assays comprise an application zone adapted to receive a liquid sample, a reagent zone spaced laterally from and in fluid communication with the application zone, and a detection zone spaced laterally from and in fluid communication with the reagent zone. The reagent zone can comprise a compound (e.g. an antibody) that is mobile in the liquid and capable of interacting with an analyte in the sample, e.g., to form an analyte-reagent complex, and/or with a molecule bound in the detection zone. The detection zone may comprise a binding molecule (e.g. an antibody) that is immobilized on the strip and is capable of interacting with the analyte and/or the reagent and/or an analyte-reagent complex to produce a detectable signal. Such assays can be used to detect an analyte in a sample through direct (sandwich assay) or competitive binding. Examples of lateral flow devices are provided in U.S. Pat. Nos. 6,194,220, 5,998,221 and 5,798,273.

TABLE 1

Sequences

| ANTIBODY-ID/SEQ-ID NUMBER | REGION | SEQUENCE |
|---|---|---|
| AdaTNF#1 | VH1A | |
| | VLκ3 | |
| SEQ ID NO: 1 (Kabat) | HCDR1 | GGTFSTYAIS |
| SEQ ID NO: 2 (Kabat) | HCDR2 | WMGGIIPIFGTANYAQKFQG |
| SEQ ID NO: 3 (Kabat) | HCDR3 | DYFSSIGWVVYYGPMDY |
| SEQ ID NO: 4 (Kabat) | LCDR1 | RASQSVSSPYLA |
| SEQ ID NO: 5 (Kabat) | LCDR2 | LLIYDVSSRAT |

TABLE 1-continued

Sequences

| ANTIBODY-ID/SEQ-ID NUMBER | REGION | SEQUENCE |
|---|---|---|
| SEQ ID NO: 6 (Kabat) | LCDR3 | QQYTSTPP |
| SEQ ID NO: 7 | VL | DIVLTQSPATLSLSPGERATLSCRASQSVSSPYLAWY QQKPGQAPRLLIYDVSSRATGIPARFSGSGSGTDFTLT ISSLEPEDFAVYYCQQYTSTPPTFGQGTKVEIKRT |
| SEQ ID NO: 8 | VH | QVQLVQSGAEVKKPGSSVKVSCKASGGTFSTYAISW VRQAPGQGLEWMGGIIPIFGTANYAQKFQGRVTITAD ESTSTAYMELSSLRSEDTAVYYCARDYFSSIGWVVYY GPMDYWGQGTLVTVSS |
| SEQ ID NO: 9 | DNA VL | gatatcgtgctgacccagagcccggcgaccctgagcctgagcccgggtga acgtgccaccctgagctgcagagcgagccagtctgtttcttctccgtacctgg cttggtaccagcagaaaccgggccaggccccgcgtctattaatctacgacg tttcttctcgtgcgaccggcattccggcgcgttttagcggcagcggatccggc accgatttcaccctgaccattagcagcctggaaccggaagactttgcggtgt attattgccagcagtacacttctactccgccgacctttggccagggcacgaa agttgaaattaaacgtacg |
| SEQ ID NO: 10 | DNA VH | caggtgcaattggtgcagagcggtgccgaagtgaaaaaaccgggcagca gcgtgaaagttagctgcaaagcatccggagggacgttttctacttacgctatc tcttgggtgcgccaggcccgggccagggcctcgagtggatgggcggtatc atcccgatcttcggcactgcgaactacgcccagaaatttcagggccgggtg accattaccgccgatgaaagcaccagcaccgcctatatggaactgagcag cctcgcagcgaagatacgccgtgtattattgcgcgcgtgactacttctcttc tatcggttggttgtttactacggtccgatggattactggggccaaggcaccct ggtgactgttagctca |
| AdaTNF#5 | | VH1A<br>VLκ1 |
| SEQ ID NO: 11 (Kabat) | HCDR1 | GGTFSTNAIS |
| SEQ ID NO: 12 (Kabat) | HCDR2 | WMGGINPHLGHADYAQKFQG |
| SEQ ID NO: 13 (Kabat) | HCDR3 | GWYYIGSNPSMYPNYFDP |
| SEQ ID NO: 14 (Kabat) | LCDR1 | RASQTISSYLN |
| SEQ ID NO: 15 (Kabat) | LCDR2 | LLIYTASNLQS |
| SEQ ID NO: 16 (Kabat) | LCDR3 | QQVLHLPH |
| SEQ ID NO: 17 | VL | DIQMTQSPSSLSASVGDRVTITCRASQTISSYLNWYQ QKPGKAPKLLIYTASNLQSGVPSRFSGSGSGTDFTLTI SSLQPEDFATYYCQQVLHLPHTFGQGTKVEIKRT |
| SEQ ID NO: 18 | VH | QVQLVQSGAEVKKPGSSVKVSCKASGGTFSTNAISW VRQAPGQGLEWMGGINPHLGHADYAQKFQGRVTITA DESTSTAYMELSSLRSEDTAVYYCARGWYYIGSNPSM YPNYFDPWGQGTLVTVSS |
| SEQ ID NO: 19 | DNA VL | gatatccagatgacccagagcccgagcagcctgagcgccagcgtgggcg atcgcgtgaccattacctgcagagccagccagactatttcttcttacctgaact ggtaccagcagaaaccgggcaaagcgccgaaactattaatctacactgctt ctaacctgcaaagcggcgtgccgagccgctttagcggcagcggatccggc accgatttcaccctgaccattagctctctgcaaccggaagactttgcgaccta ttattgccagcaggttctgcatctgccgcatacctttggccagggcacgaaag ttgaaattaaacgtacg |

TABLE 1-continued

Sequences

| ANTIBODY-ID/SEQ-ID NUMBER | REGION | SEQUENCE |
|---|---|---|
| SEQ ID NO: 20 | DNA VH | Caggtgcaattggtgcagagcggtgccgaagtgaaaaaaccgggcagc agcgtgaaagttagctgcaaagcatccggagggacgttttctactaacgcta tctcttgggtgcgccaggccccgggccagggcctcgagtggatgggcggta tcaacccgcatctgggccatgcggactacgcccagaaatttcagggcgg gtgaccattaccgccgatgaaagcaccagcaccgcctatatggaactgag cagcctgcgcagcgaagatacggccgtgtattattgcgcgcgtggttggtac tacatcggttctaacccgtctatgtacccgaactacttcgatccgtggggcca aggcaccctggtgactgttagctca |
| IFX-TNF#1 | | VH3-23 VLκ3 |
| SEQ ID NO: 21 (Kabat) | HCDR1 | GFTFSSYGMH |
| SEQ ID NO: 22 (Kabat) | HCDR2 | WVSYIYYGGSDTYYADSVKG |
| SEQ ID NO: 23 (Kabat) | HCDR3 | GMYYLYDQPAFDY |
| SEQ ID NO: 24 (Kabat) | LCDR1 | SGDNIRSDYVH |
| SEQ ID NO: 25 (Kabat) | LCDR2 | LVIYDKSERPS |
| SEQ ID NO: 26 (Kabat) | LCDR3 | QAADTWSTIV |
| SEQ ID NO: 27 | VL | DIELTQPPSVSVAPGQTARISCSGDSLGDYVHWYQQ KPGQAPVLVIYADNNRPSGIPERFSGSNSGNTATLTIS GTQAEDEADYYCQTYDDRSSPVFGGGTKLTVLGQ |
| SEQ ID NO: 28 | VH | QVQLVESGGGLVQPGGSLRLSCAASGFTFNSYAMSW VRQAPGKGLEWVSGIGSYTYYADSVKGRFTISRDNSK NTLYLQMNSLRAEDTAVYYCARLSQTGVMDYWGQGT LVTVSS |
| SEQ ID NO: 29 | DNA VL | gatatcgaactgacccagccgccttcagtgagcgttgcaccaggtcagacc gcgcgtatctcgtgtagcggcgattctcttggtgattattatgttcattggtacca gcagaaacccgggcaggcgccagttcttgtgatttatgctgataatcgtc cctcaggcatcccggaacgctttagcggatccaacagcggcaacaccgcg accctgaccattagcggcactcaggcggaagacgaagcggattattattgc cagacttatgatgatcgttcttctcctgtgtttggcggcggcacgaagttaacc gtcctaggtcag |
| SEQ ID NO: 30 | DNA VH | caggtgcaattggtggaaagcggcggcggcctggtgcaaccgggcggca gcctgcgtctgagctgcgcggcctccggatttacctttaattcttatgctatgtctt gggtgcgccaagcccctgggaagggtctcgagtgggtgagcggtatcggt agctataccattatgcggatagcgtgaaaggccgttttaccatttcacgtgat aattcgaaaaacaccctgtatctgcaaatgaacagcctgcgtgcggaagat acggccgtgtattattgcgcgcgtctttctcagactggtgttatggattattgggg ccaaggcaccctggtgacggttagctca |

EXAMPLES

Generation of Fab Fragments and Antibodies that are Specific for an Antibody/Antigen Complex For the selection of antibodies specifically recognizing the antibody/antigen complex a commercially available phage display library, the MorphoSys HuCAL PLATINUM® library was used. Said antibody library is based on the HuCAL® concept (Knappik et al., (2000) J Mol Biol 296:57-86) and employs the CysDisplay® technology for displaying the Fab on the phage surface (WO2001/05950 to Lohning). However, any other available antibody library would be suitable to identify complex-specific antibodies.

To identify antibody/antigen complex antibodies specific panning strategies had been developed to target antibody/antigen complexes. Thereby recombinant, purified antigen and its respective recombinant therapeutic antibody were used for the panning. According to the described examples below, for 3 different antibody/antigen complexes, antibodies that only bind to that specific complex were identified. All described panning strategies and antigens were used for the antibody selection process. Each panning strategy comprised of at least 3 individual rounds of panning and contained unique antigens, antigen concentrations and washing stringency.

Example 1: Generation and Characterization of Fab Fragments and Antibodies that are Specific for the Adalimumab/TNF-α Complex To identify antibodies which specifically bind to the Adalimumab/TNF-α complex recombinant TNF-α (BioLegend 570108, Lot B137143) coupled to magnetic beads and Adalimumab were used as antigens for a solution panning approach.

a) Panning

For the solution panning TNF-α was coupled covalently to the Epoxy M-450 magnetic beads (Dynabeads M-450, Dynal) and the phage preparation of a phage display antibody library are washed and blocked with Chemiblocker (Chemicon).

To provide Adalimumab/TNF-α complexes the recombinant TNF-α which was coupled to magnetic beads was pre-incubated with Adalimumab. For the first panning round, in the presence of Chemiblocker (Chemicon) and Tween/PBS, phage-antibodies were added to the Adalimumab/TNF-α complexes in the presence of purified human IgG1kappa (50 µg/mL), 10% human serum, 50 µg/ml Rituximab (IgG1kappa) and 1 µg/ml TNF-α to adsorb all phage-antibodies which are specific to IgG1kappa and free TNF-α or that cross-react with any components of human serum. After incubation on a rotator over night at 2 to 8° C. the phage-antigen mixture was transferred to tubes and the magnetic beads were captured using a magnetic separator. The supernatant was carefully removed from the beads and remaining beads were washed PBST.

Subsequent panning round 2 and 3 were performed in a similar fashion with increasing concentrations of free TNF-α (5 µg/ml in 2nd panning round; 25 µg/ml in 3rd panning round) to increase stringency and discard antibodies which cross-react to free TNF-α.

Upon each round of panning the remaining phages were eluted, and eluted phages were used immediately for infection of *E. coli* TG1 bacteria. After rescue of the phages by using helper phage the polyclonal amplified phage output was titered again and used in consecutive selection steps. After the 3rd round of panning the DNA of the eluted antigen-specific phages was isolated from the infected bacteria and the Fab-encoding DNA was subcloned via PCR into specific Fab expression vectors. After transformation of TG1-F bacteria, using the Fab-encoding vectors, single clone expression and preparation of periplasmic extracts containing HuCAL-Fab fragments were performed. Fab-containing periplasmic extracts were used for the initial screening and characterization.

For further characterization purified Fabs had been used. Expression of Fab fragments in TG-1 cells was carried out in shaker flask cultures using 500 ml of 2× YT medium supplemented with 1 mM chloramphenicol and 0.1% glucose. Expression was induced by addition of 0.75 mM IPTG for 20 h at 30° C. Cells were disrupted using a lysis buffer containing lysozyme, Bugbuster and Benzonase and Fab fragments isolated by Ni-NTA chromatography (Bio-Rad, Germany). Protein concentrations were determined by UV-spectrophotometry. Purity of Fab fragments was analyzed in denatured, reduced state using SDS-PAGE and in native state by HP-SEC.

In order to express full length IgGs, variable domain fragments of heavy (VH) and light chains (VL) were subcloned from Fab expression vectors into appropriate pMORPH®_hIg vectors for human IgG2, human IgG4, human IgG4_Pro, and human IgG1f LALA.

b) Screening

Primary screening was done by ELISA. 368 clones were randomly picked from the output of the above described panning procedure and grown in the 384 well ELISA plates. After induction of antibody expression (0.75 mM IPTG for 20 h at 30° C.) and lysis of the cells by using lysozyme, the cell lysates containing the antibodies were tested in ELISA.

Therefore the following antigens, Adalimumab/TNF-α complex, purified human IgG1/kappa from myeloma cell line; Rituximab and free recombinant TNF-α were coated on an ELISA plate.

Altogether 12 clones that were positive (signal at least 5-fold over background) on the complex but did not bind to the other antigens were identified. Thereupon the 12 clones were sequenced to identify unique antibodies. Seven unique sequences could be identified. These 7 clones were expressed and purified and were then characterized.

c) Characterization

First the 7 antibodies were tested for specific binding in an ELISA against a series of unrelated and related antigens and the Adalimumab/TNF-α complex, wherein either Adalimumab was coated on the plate and TNF-α was subjected for the formation of the complex or the other way around. Therefore 5 µg/mL of each of the antigens were coated on a microtiter plate over night. After washing and blocking with 5% BSA, anti-Adalimumab/TNF-α antibodies in Fab-FH format (20 µL from a 2 µg/mL solution) were added. Detection was performed using an HRP-labeled anti-His antibody and QuantaBlu fluorogenic peroxidase substrate. AdaTNF #1 and AdaTNF #5 proofed to be highly specific for the complex (FIG. 1).

Figure 2:
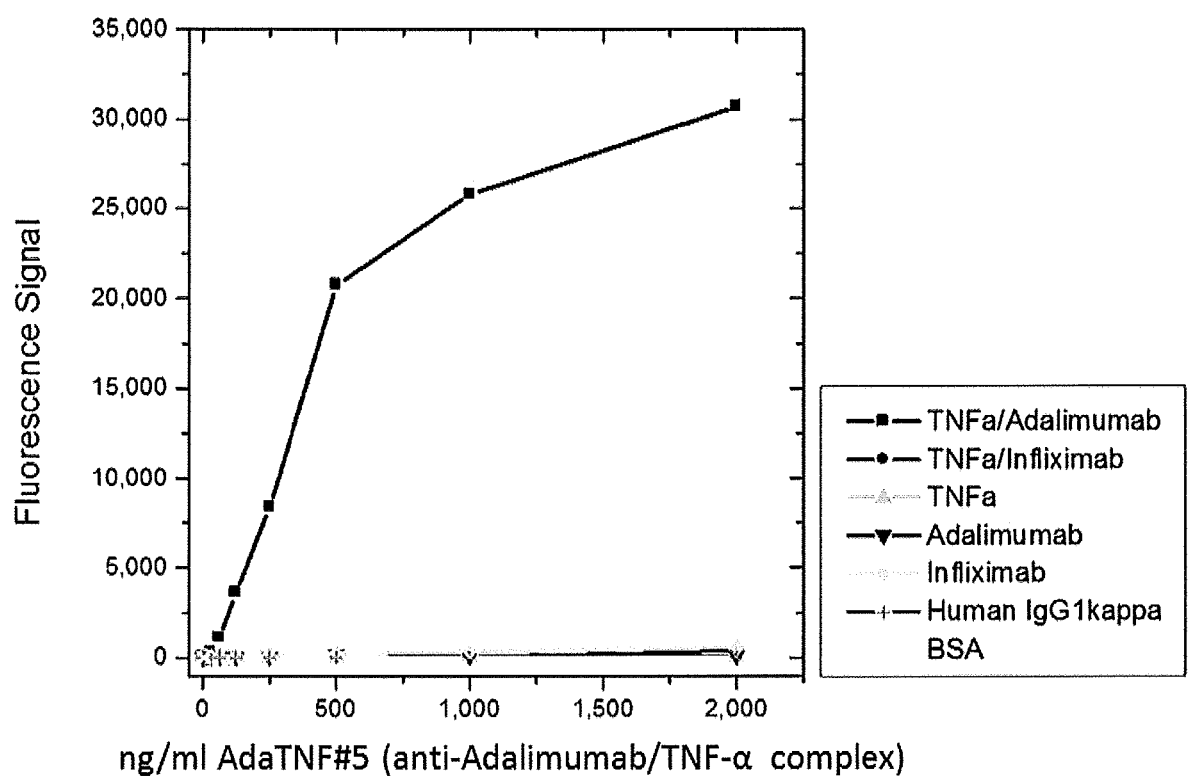
FIG. 2 depicts the results of a titration of AdaTNF #5 on different immobilized antigens in ELISA. Over the concentration range tested (0.03 to 2000 ng/mL), AdaTNF #5 bound only to the Adalimumab/TNF-α complex but not to its single components and other antigens.

In a next step, AdaTNF #5 was tested in more detail by titrating the antibody on different immobilized antigens. Over the concentration range tested (0.03 to 2000 ng/mL), the antibody bound only to the Adalimumab/TNF-α complex but not to an infliximab/TNF-α complex, not to unbound Adalimumab or free TNF-α, and not to other antigens (FIG. 2)

Figure 3:
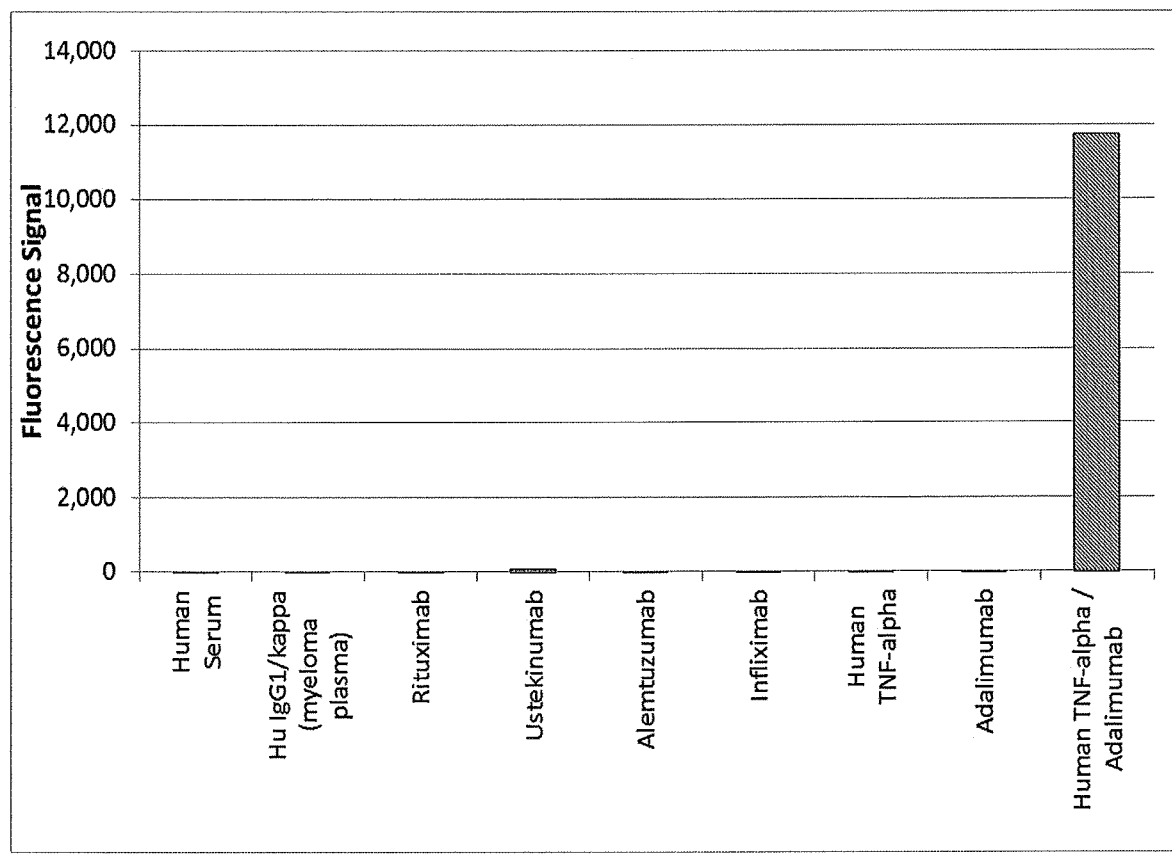
FIG. 3 depicts results of purified AdaTNF #5 converted into a full length human IgG1 tested on various antigens in ELISA. Purified AdaTNF #5-hIgG1 conjugated to HRP specifically binds complex of Adalimumab and TNF-α.

AdaTNF #5 was converted into a full length human IgG1 format, expressed in a human cell line and purified via protein A chromatography for further analysis. First it was tested whether the antibody in (bivalent) IgG1 format still shows the same specificity. Antigens were coated at 5 µg/mL on a microtiter plate over night. After washing and blocking with 5% BSA, HRP-conjugated AdaTNF #5-hIgG1 (20 µL from a 2 µg/mL solution in HiSpec buffer) was added. Detection was performed using the QuantaBlu® fluorogenic peroxidase substrate. Purified AdaTNF #5-hIgG1 conjugated to HRP specifically binds complex of Adalimumab and TNF-α. (FIG. 3)

Figure 4:
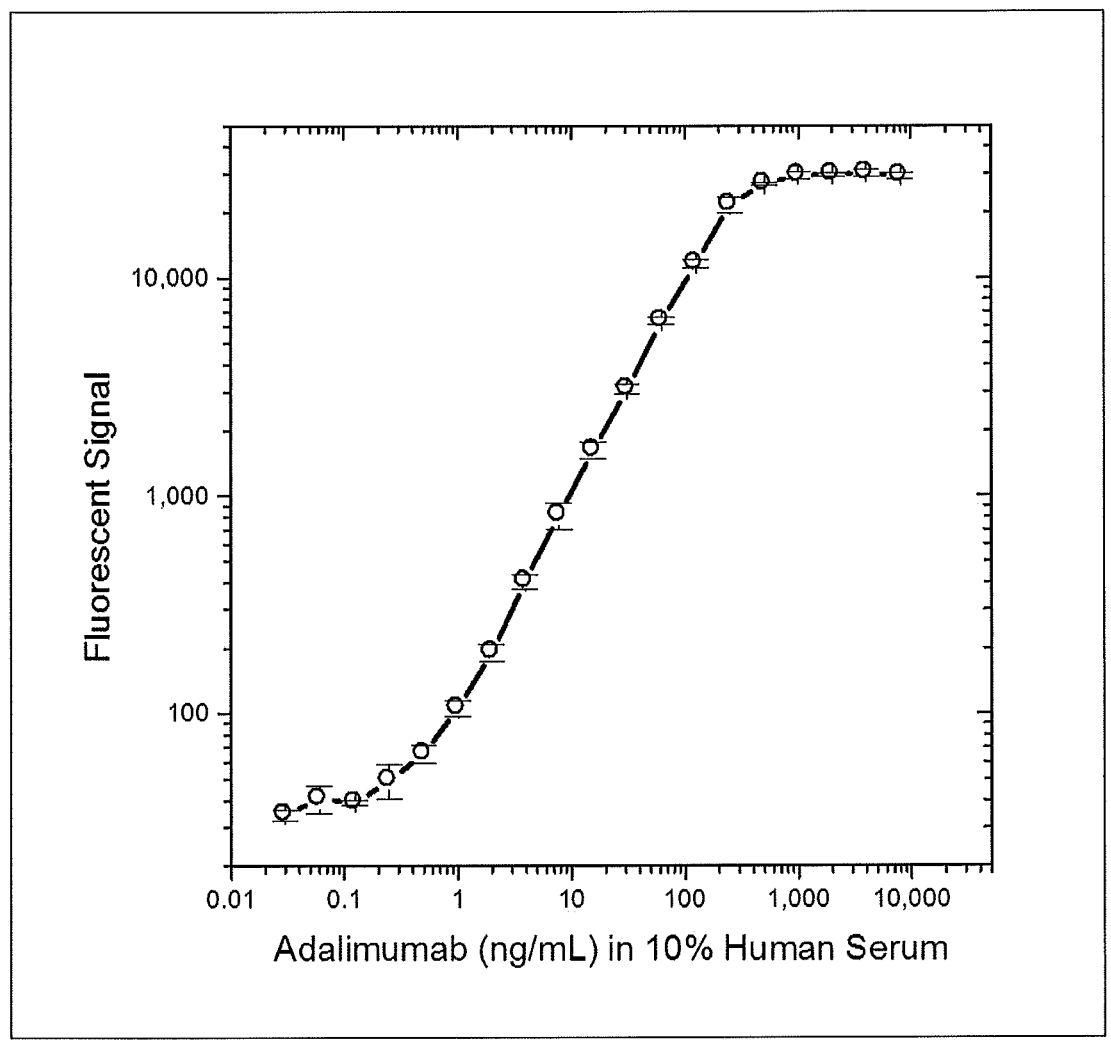
FIG. 4 depicts results of a pharmacokinetic ELISA assay. Human TNF-α was coated on a microtiter plate and increasing concentrations of Adalimumab were spiked into 10% human serum and were applied to the pre-coated plate. After washing, the anti-Adalimumab/TNF-α hIgG1 antibody AdaTNF #5 (conjugated to HRP) was added at 2 µg/ml. Detection was performed by adding QuantaBlu® fluorogenic peroxidase substrate. AdaTNF #5 bound to Adalimumab/TNF-α complex in a dose-dependent fashion in the presence of human serum.

For further characterization, the monovalent intrinsic affinity of AdaTNF #5 was measured as kD=67 nM by real time, label free molecular interaction analysis using an Attana A200 instrument on an immobilized Adalimumab-TNF-α complex. It was then tested whether the complex specific antibody AdaTNF #5 can be used to determine Adalimumab spiked in human serum. Human TNF-α was coated at 5 µg/mL on a microtiter plate and incubated over night. After washing and blocking with 5% BSA in PBST, increasing concentrations of Adalimumab were spiked into 10% human serum and were applied to the pre-coated plate. After washing, the anti-Adalimumab/TNF-α hIgG1 antibody AdaTNF #5 (conjugated to HRP) was added at 2 µg/mL. Detection was performed by adding QuantaBlu® fluorogenic peroxidase substrate. AdaTNF #5 bound to Adalimumab/TNF-α complex in a dose-dependent fashion (FIG. 4). Therefore, this novel specificity can be used to develop highly sensitive quantification assays that are not dependent on the most often used bridging format.

Example 2: Generation and Characterization of Fab Fragments and Antibodies that are Specific for the Infliximab/TNF-α Complex To identify antibodies which specifically bind to the Infliximab/TNF-α complex recombinant TNF-α (BioLegend 570108, Lot B137143) coupled to magnetic beads and Infliximab were used as antigens for a solution panning approach.

Panning and screening was performed as described in Example 1. Upon primary screening 3 unique antibodies were identified to bind to the Infliximab/TNF-α complex and were expressed, purified and subjected to further characterization studies.

Figure 5:
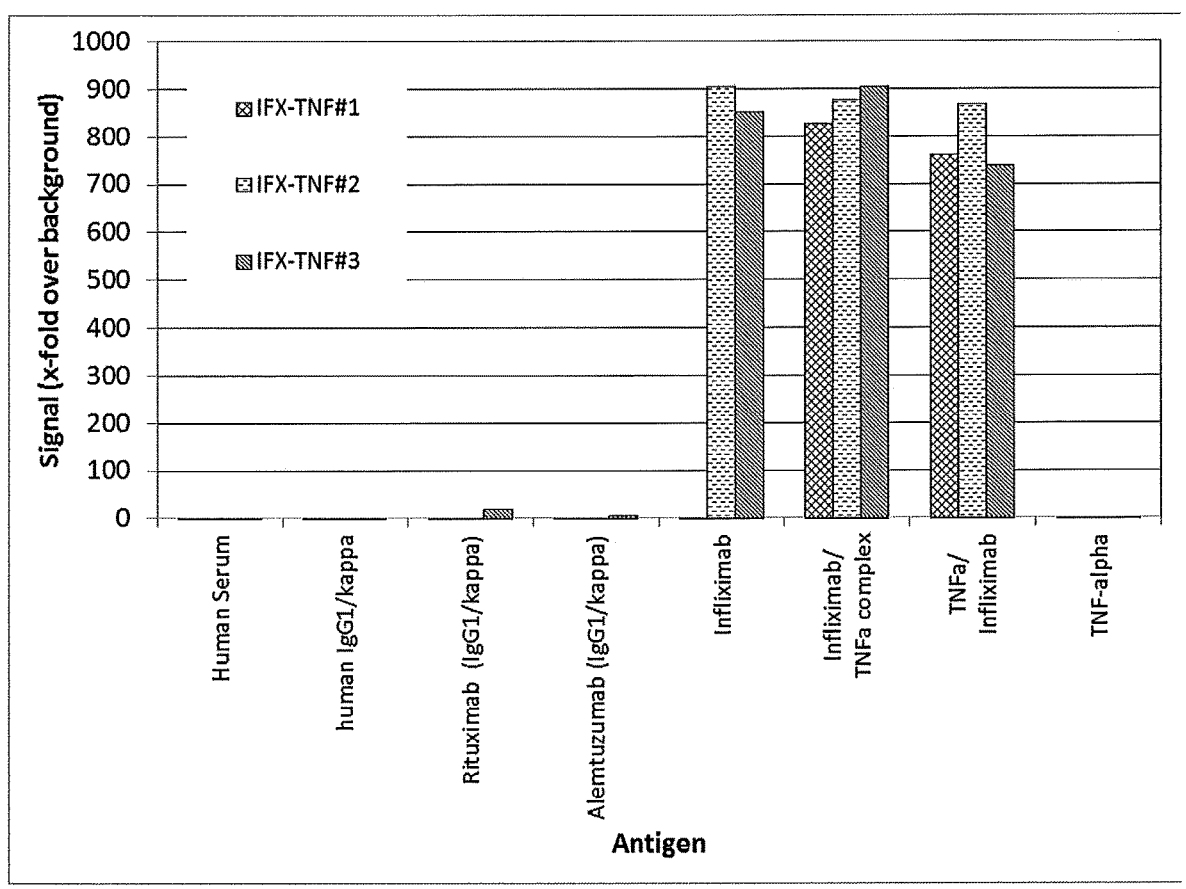
FIG. 5 depicts results of IFX-TNF #1, IFX-TNF #2 and IFX-TNF #3 tested on various antigens in ELISA. Therefore 5 µg/mL of each of the antigens were coated on a microtiter plate and anti-Infliximab/TNF-α antibodies in Fab-FH format (20 µL from a 2 µg/mL solution) were added. IFX-TNF #1 proofed to specifically detect the Infliximab/TNF-α complex (FIG. 5).

IFX-TNF #1, IFX-TNF #2 and IFX-TNF #3 were tested for specific binding in an ELISA against a series of unrelated and related antigens and the Infliximab/TNF-α complex. Therefore 5 µg/mL of each of the antigens were coated on a microtiter plate over night. After washing and blocking with 5% BSA, anti-Infliximab/TNF-α antibodies in Fab-FH format (20 µL from a 2 µg/mL solution) were added. Detection was performed using an HRP-labeled anti-His antibody and QuantaBlu fluorogenic peroxidase substrate. IFX-TNF #1 proofed to be highly specific for the complex (FIG. 5).

Example 3: Generation and Characterization of Fab Fragments and Antibodies that are Specific for the MOR103/GM-CSF Complex To identify antibodies which specifically bind to the MOR103/GM-CSF complex recombinant biotinylated human GM-CSF and MOR103 were used as antigens for a solid phase panning approach.

a) Panning

According to the panning procedures as described in Example 1 the phage preparations were prepared.

To provide MOR103/GM-CSF complexes the recombinant GM-CSF was immobilized on a streptavidin coated plate and MOR103 was added for the formation of complexes.

All 3 rounds of panning were performed in the presence of 100 µg/ml of MOR3207 (lysozyme specific human IgG1) and 5 µg/ml of free GM-CSF. As described in Example 1 the DNA of the isolated phages were subcloned into Fab-expression vectors and respective clones were subjected to primary screening.

b) Screening

Primary screening was done by ELISA. 368 clones were randomly picked from the output of the above described panning procedure and grown in the 284 well ELISA plates. After induction of antibody expression (0.75 mM IPTG for 20 h at 30° C.) and lysis of the cells by using lysozyme, the cell lysates containing the antibodies were tested in ELISA.

Therefore the following antigens, MOR103/GM-CSF complex, purified human MOR3207 (IgG1/kappa); MOR103 and free recombinant human GM-CSF were coated on an ELISA plate.

Altogether 3 unique clones that were positive (signal at least 5-fold over background) on the complex but did not bind to the other antigens were identified. Thereupon selected clones were expressed and purified and were tested for specific binding in an ELISA against a series of unrelated and related antigens and the MOR103/GM-CSF complex.

5 µg/mL of each of the antigens (BSA, GST, MOR03207 and MOR103) were coated on a microtiter plate over night. For the immobilisation of biotinylated GM-CSF (GM-CSF-bio), Neutravidin was coated at 5 µg/mL over night and after blocking with 5% BSA GM-CSF-bio was added. The respective MOR103/GM-CSF-bio complex was formed by adding MOR103 at 5 µg/ml to the immobilised GM-CSF-bio. After washing and blocking with 5% BSA, anti MOR103/GM-CSF antibodies in Fab format containg a C-terminal 6-His tag (20 µL from a 2 µg/mL solution) were added, detected thereafter using an anti-His detection antibody and quantified after washing using QuantaBlu fluorogenic peroxidase substrate.

Figure 6:
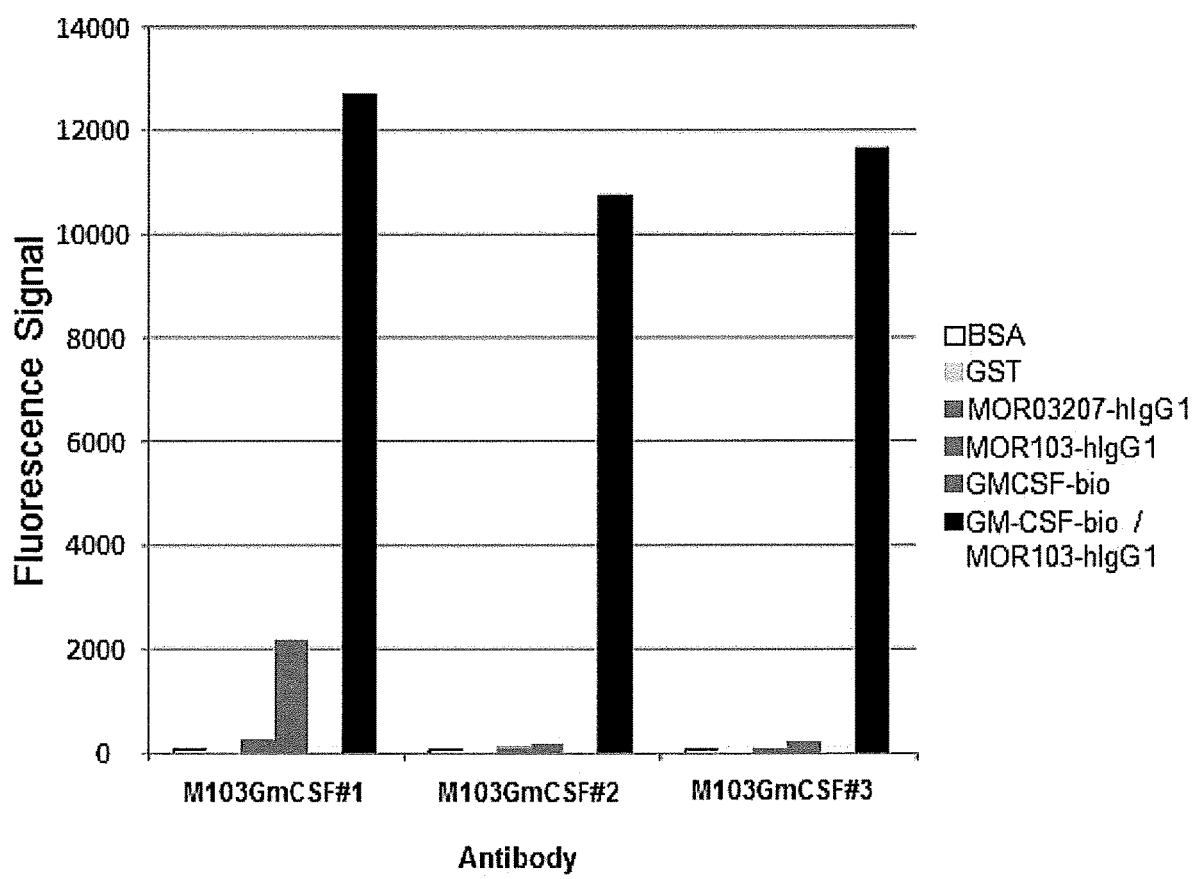
FIG. 6 depicts results of a screening ELISA to detect anti-MOR103/GM-CSF complex antibodies. 5 µg/mL of each of the antigens (BSA, GST, MOR03207 and MOR103) were coated on a microtiter plate. Furthermore MOR103/GM-CSF complex was immobilized on the plate as well. M103GmCSF #1, M103GmCSF #2 and M103GmCSF #3 specifically detect the MOR103/GM-CSF complex but not GM-CSF or MOR103 alone.

All 3 antibodies (M103GmCSF #1, M103GmCSF #2, and M103GmCSF #3) turned out to specifically detect the MOR103/GM-CSF complex but not GM-CSF or MOR103 alone (FIG. 6). Some binding of M103GmCSF #1 to MOR103 was observed but could not be confirmed in a subsequent titration ELISA.

c) Characterization

Figure 7:
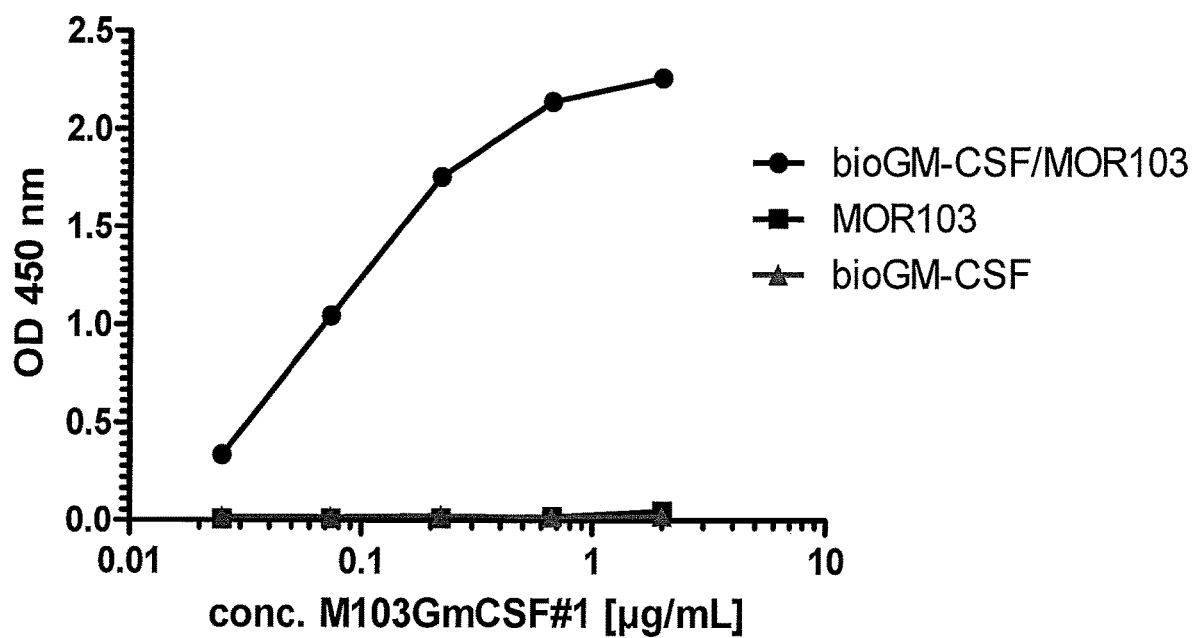
FIG. 7 depicts results of an ELISA testing M103GmCSF #1 for target selectivity. Either MOR103 alone, the biotinylated GM-CSF or the biotinylated GM-CSF bound to MOR103 were coated on an Avidin-coated plate. His-tagged M103GmCSF #1 Fab was added in increasing concentrations and was detected. M103GmCSF #1 showed high selectivity for binding to the drug-target complex and not to the individual proteins (drug and target).

M103GmCSF #1 was further characterized. Either MOR103 alone, the biotinylated GM-CSF or the biotinylated GM-CSF bound to MOR103 were coated on an Avidin-coated plate. His-tagged M103GmCSF #1 Fab was added in increasing concentrations and was detected using a His-specific POD conjugated secondary antibody and quantified using QuantaBlu fluorogenic peroxidase substrate. M103GmCSF #1 showed high selectivity for binding to the drug-target complex and not to the individual proteins (drug and target) (FIG. 7). Monovalent affinity of M103GmCSF #1 Fab to drug-target complex: kD=4.9 nM.

Example 4: Assay to Detect Antibody/Antigen Complex in Human Sera Using an Antibody Specific for the Complex of a Cognate Antibody and its Antigen To monitor and quantify specific antibody/antigen complexes from human sera or plasma a robust pharmacokinetic detection assay was established based on MSD® (Meso Scale Discovery) technology.

In brief, 2 µg/ml of rat anti-human GM-CSF solved in PBS was coated to the respective wells of a Multi-Array® 96-well plate Standard plate (Meso Scale Discovery; Cat: L11XA-3).

The next day MOR103 (hIgG1λ, DSM: P19292; CMC2; conc.: 2.0 mg/mL) and GM-CSF (Bayer; NDC50419-002-33 Lot: B16891; conc.: 0.25 mg/mL) were diluted in LCB buffer (LowCross-Buffer, Candor Bioscience GmbH Cat #100500, Lot #100C434c). To form MOR103/GM-CSF complexes MOR103 and GM-CSF were mixed in a 5:1 ratio and supplemented with 100% Human serum (pooled, male; Sigma, Cat: H4522; Lot: 11M0605). After 1 h incubation the MOR103 and GM-CSF mix was diluted 2-fold with LCB buffer leading to a final serum concentration of 50% and transferred from the pre-incubation plate to the pre-coated Multi-Array® 96-well plate and further incubated for 1 h at room temperature. The assay plate was washed using PBST and 400 ng/ml of ECL-labelled M103GmCSF #1 IgG (Lot: 110801_11STE11*1; ECL-labelling: Lot: 110831_5AUN51; conc.:1.7 mg/mL in PBS) was added for 1 h to detect MOR103/GM-CSF complexes and was subsequently quantified using MSD read buffer T (Cat: R92TC-1) and measured in a MSD Sector Imager 6000 (Meso Scale Discovery, Gaithersburg, Md., USA).

Figure 8:
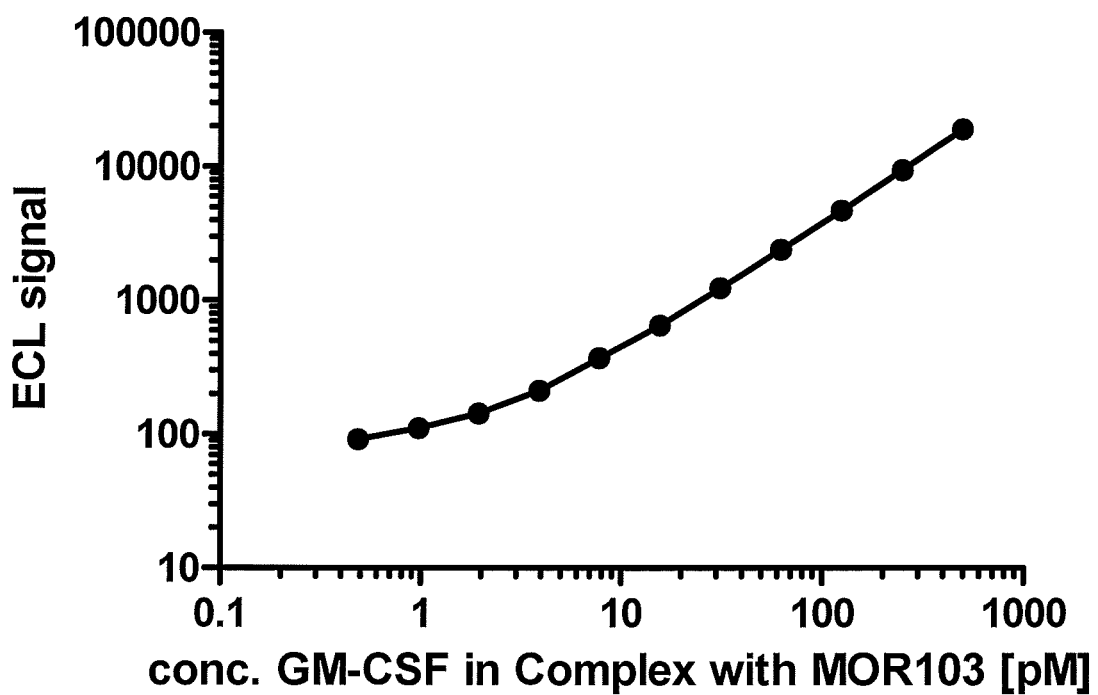
FIG. 8 depicts results of a MSD® (Meso Scale Discovery) based ligand binding assay to quantify MOR103/GM-CSF complexes in human serum. MOR103/GM-CSF complexes were supplemented with human serum and titrated on a Multi-Array® 96-well plate Standard plate. ECL-labeled M103GmCSF #1 IgG was used to detect the MOR103/GM-CSF complexes. Throughout the titration curve the MOR103/GM-CSF complexes were specifically detected in the presence of 50% human sera in a dose-dependent manner.

Throughout the titration curve the MOR103/GM-CSF complexes were specifically detected in the presence of human sera in dose-dependent manner and with a back accuracy to a fitted curve of at least 96-104% for each of the concentrations (see below, FIG. 8)

| Calibration Sample | Nominal Conc. [pM] | Precission Duplikate Analysis [%] | Accuracy [%] |
| --- | --- | --- | --- |
| St01 | 500 | 2.3 | 100.3 |
| St02 | 250 | 0.5 | 99.5 |
| St03 | 125 | 0.4 | 99.5 |
| St04 | 62.5 | 3.1 | 100.2 |
| St05 | 31.25 | 3.3 | 100.4 |
| St06 | 15.63 | 2.2 | 99.7 |
| St07 | 7.81 | 2.8 | 103.7 |
| St08 | 3.91 | 2.6 | 96.5 |
| St09 | 1.95 | 4.1 | 97.3 |
| St10 | 0.98 | 0 | 104.8 |
| St11 | 0.49 | 20 | 99.8 |

The disclosure having been fully described, it is further illustrated by the following examples and claims, which are illustrative and are not meant to be further limiting.

The foregoing written specification is considered to be sufficient to enable one skilled in the art to practice the disclosure. It will be appreciated, however, that no matter how detailed the foregoing may appear in text, the disclosure may be practiced in many ways and the disclosure should be construed in accordance with the appended claims and any equivalents thereof.

The invention claimed is:

1. A method to identify an isolated monoclonal antibody, or functional fragment thereof which specifically binds to a complex of a specific cognate antibody and its antigen and does not bind either said cognate antibody or said antigen alone, said method comprising
   (a) screening a library of antibodies or antibody fragments against a complex of a specific with against the complex of the specific cognate antibody and its antigen in the presence of the unbound antigen and an antibody different from the specific cognate antibody that has the same isotype as the specific cognate antibody,
   (b) isolating a complex of the specific of a specific cognate antibody and its antigen and the bound antibodies or antibody fragments, and
   (c) identifying and isolating said bound antibodies or antibody fragments,
   wherein screening of the library of antibodies or antibody fragments against the complex of the specific cognate antibody and its antigen is performed in the presence of the unbound antigen and the antibody different from the specific cognate antibody that has the same isotype and framework as the specific cognate antibody.

2. The method according to claim 1, wherein the epitope of said isolated monoclonal antibody or fragment thereof includes one or more amino acids of a variable region of the specific cognate antibody.

3. The method according to claim 1, wherein said isolated monoclonal antibody or fragment thereof is a humanized or human monoclonal antibody or fragment.

4. The method according to claim 1, wherein the antigen is a cytokine or a receptor.

5. The method according to claim 1, wherein said specific cognate antibody is a murine, chimeric, humanized or human monoclonal antibody or fragment thereof.

6. The method according to claim 5, wherein the specific cognate antibody or fragment thereof is selected from the group consisting of Adalimumab, MOR103, Rituximab, Trastuzumab, Alemtuzumab, Bevacizumab, Cetuximab, Gemtuzumab, Infliximab, Ranibizumab, Ustekinumab, Golimumab, Natalizumab, Ofatumumab, Omalizumab and Panitumumab.

* * * * *